(12) United States Patent
Csaky et al.

(10) Patent No.: US 8,039,585 B2
(45) Date of Patent: Oct. 18, 2011

(54) THERAPEUTIC ADMINISTRATION OF THE SCRAMBLED ANTI-ANGIOGENIC PEPTIDE C16Y

(75) Inventors: Karl G. Csaky, Kensington, MD (US); Hynda Kleinman, Kensington, MD (US); Lourdes Ponce, Germantown, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1003 days.

(21) Appl. No.: 10/588,884

(22) PCT Filed: Feb. 12, 2004

(86) PCT No.: PCT/US2004/004142
§ 371 (c)(1),
(2), (4) Date: Aug. 27, 2007

(87) PCT Pub. No.: WO2005/087250
PCT Pub. Date: Sep. 22, 2005

(65) Prior Publication Data
US 2008/0131430 A1    Jun. 5, 2008

(51) Int. Cl.
| | |
|---|---|
| *A61K 38/04* | (2006.01) |
| *A61K 38/00* | (2006.01) |
| *A61K 51/00* | (2006.01) |
| *A61P 35/00* | (2006.01) |
| *C07K 5/00* | (2006.01) |
| *C07K 7/00* | (2006.01) |
| *C07K 16/00* | (2006.01) |
| *C07K 17/00* | (2006.01) |

(52) U.S. Cl. ....... 530/328; 530/327; 530/300; 514/19.2; 424/1.69

(58) Field of Classification Search .................. None
See application file for complete search history.

(56) References Cited

U.S. PATENT DOCUMENTS
6,121,236 A    9/2000  Ben-Sasson
6,667,388 B2   12/2003 Bein et al.

OTHER PUBLICATIONS

Ciulla, T.A. 2003. Recent advances in the treatment of exudative age-related macular degeneration, including transpupillary thermotherapy. Acta Opthalmol Scand 81:103-104.
Grant, D.S., et al. 1989. Two different laminin domains mediate the differentiation of human endothelial cells into capillary-like structures in vitro. Cell 58:933-943.
Iwamoto, Y., et al. 1987. YIGSR a pentapeptide from the B1 chain of laminin inhibits tumor cell metastases. Science 238:1132-1134.
Kuratomi, Y., et al. 2002. Laminin γ1 chain peptide, C-16 (KAFDITYVRLKF), promotes migration, MMP-9 secretion, and pulmonary metastasis of B16-F10 mouse melanoma cells. Br J Cancer 86:1169-1173.
Kuratomi, Y., et al. 1999. Identification of metastasis-promoting sequences in the mouse laminin α-1 chain. Exp Cell Res 249:386-395.
Malinda, K. M., et al. 1999. Identification of laminin α-1 and β-1 chain peptides active for endothelial cell adhesion, tube formation, and aortic sprouting. FASEB J 13:53-62.
Ponce, M. L., et al. 1999. Identification of endothelial cell binding sites on the laminin γ-1 chain. Circ Res 84:688-694.
Ponce, M. L., Nomizu, M., Kleinman, H. K. 2001. An angiogenic laminin site and its antagonist bind through the αvβ3 and α5β1 integrins. FASEB J 15:1389-1397.
Ponce, M. L., Kleinman, H. K. 2003a. Identification of Redundant Angiogenic sites in laminin α1 and γ1 chains. Exp Cell Res 285:189-195.
Ponce, M.L., et al. 2003b. Identification of a potent peptide antagonist to an active laminin-1 sequence that blocks angiogenesis and tumor growth. Cancer Res 63:5060-5064.
Powell, S.K., Kleinman, H.K. 1997. Neuronal laminins and their cellular receptors. Int J Biochem Cell Biol 29:401-414.
Pupa, S.M., Menard, S., Forti, S., Tagliabue, E. 2002. New insights into the role of extracellular matrix during tumor onset and progression. J Cellul Physiol 192:259-267.
Sakamoto, N., Iwahana, M., Tanaka, N.G., Osada, Y. 1991. Inhibition of angiogenesis and tumor growth by a synthetic laminin peptide, CD PGYIGSR-NH2. Cancer Res 51:903-906.
Varner, J.A., Cheresh, D.A. 1996. Tumor angiogenesis and the role of vascular cell integrin α v β3. Important Adv Oncol 69-87.
Auerbach, R. et al., "Expression of Organ-Specific Antigens on Capillary Endothelial Cells," Microvascular Research, no month available, 1985, 29:401-411.
Brooks, P. et al., "Requirement of Vascular Integrin $\alpha_v\beta_3$ for Angiogenesis," Science (Wash DC), Apr. 22, 1994, 264:569-571.
Burgeson, R. et al., "A New Nomenclature for the Laminins," Matrix Biology, No month available, 1994, 14:209-211.
C-elegans Sequencing Consortium, "Genome Sequence of the Nematode C. *elegans*: A Platform for Investigating Biology," Science, Dec. 11, 1998, 282(5369), 2012-2018.

(Continued)

*Primary Examiner* — Maury Audet
(74) *Attorney, Agent, or Firm* — Woodcock Washburn LLP

(57) ABSTRACT

Unregulated angiogenesis is associated with a variety of pathological conditions. Tumor growth and metastasis is dependent on the development of new blood vessels. The development of new blood vessels in the eye, or ocular neovascularization, has been implicated in a variety of serious ocular diseases. For instance, choroidal neovascularization is linked to age-related macular degeneration, while retinal neovascularization is linked to diabetic retinopathy. The present invention is based on the discovery of a peptide sequence, C16Y, which inhibits ocular neovascularization and tumor growth in vivo. C16Y is a scrambled version of the C16 peptide sequence from the γ1 chain of laminin-1. Unlike C16, which is an angiogenic stimulator, C16Y has been shown to inhibit angiogenesis. The present invention discloses methods of treating ocular neovascularization and cancer using both full-length and truncated versions of the C16Y.

20 Claims, 8 Drawing Sheets

OTHER PUBLICATIONS

Colognato, H. et al, "Form and Function: The Laminin Family of Heterotrimers," Developmental Dynamics, no month available, 2000, 218:213-234.

Fisher, C. et al., "Treatment of Septic Shock with the Tumor Necrosis Factor Receptor:Fc Fusion Protein," The Soluble TNF Receptor Sepsis Study Group, New England Journal of Medicine, Jun. 27, 1996, 334(26):1697-1702.

Folkman, J., "Angiogenesis in Cancer, Vascular, Rheumatoid and Other Diseases," Nature Medicine, no month available, Jan. 1995, 1(1):27-31.

Francis, G., "Protein Modification and Fusion Proteins," Focus on Growth Factors, no month available, 1992, 3:4-10.

Fridman, R. et al., "Reconstituted basement membrane (matrigel) and laminin can enhance the tumorigenicity and the drug resistance of small cell lung cancer cell lines," Proc Natl Acad Sci USA, Sep. 1990, 87:6698-6702.

Friedlander, M. et al., "Definition of Two Angiogenic Pathways by Distinct $\alpha_v$ Integrins," Science, (Wash DC), Dec. 1, 1995, 270:1500-1502.

Fujihara, S. et al. "A D-Amino Acid Peptide Inhibitor of NF-κB Nuclear Localization Is Efficacious in Models of Inflammatory Disease," no month available, Journal of Immunology, 2000, 165:1004-1012.

Gho, Y. et al., "Angiogenic Activity of Human Soluble Intercellular Adhesion Molecule-1," Cancer Research, Oct. 15, 1999, 59:5128-5132.

Gho, Y. et al., "Stimulation of Tumor Growth by Human Soluble Intercellular Adhesion Molecule-1," Cancer Research, May 15, 2001, 61:4253-4257.

Harvill, E. et al., "An IgG3-IL2 fusion protein activates complement, binds FcγRI, generates LAK activity and shows enhanced binding to the high affinity IL-2R," Immunotechnology, May 1995, 1(2):95-105.

Iivanainen, E. et al., "Endothelial Cell Matrix Interactions," Microscopy Research and Technology, no month available, 2003, 60:13-22.

Jaffe, E. et al., "Culture of Human Endothelial Cells Derived from Umbilical Veins. Identification By Morphologic and Immunologic Criteria," Journal of Clinical Investigation, Nov. 1973, 52:2745-2756.

Kleinman, H. et al., "Role of Basement Membrane in Tumor Growth and Metastasis," Surgical Oncology Clinics of North America, Apr. 2001, 10(2), 329-338.

Kubota, Y. et al., "Role of Laminin and Basement Membane in the Morphological Differentiation of Human Endothelial Cells into Capillary-like Structures," J Cell Biol, Oct. 1988, 107:1589-1597.

Lehoux, S. et al., "Cellular mechanics and gene expression in blood vessels," J Biomech, 2003, 36:631-643.

Maeshima, Y. et al., "Extracellular Matrix-derived Peptide Binds to $\alpha_v\beta_3$ Integrin and Inhibits Angiogenesis," Journal of Biol Chem, Aug. 24, 2001, 276(34):31959-31968.

Miner, J. et al., "The Laminin α Chains: Expression, Developmental Transitions, and Chromosomal Locations of α1-5, Identification of Heterotrimeric Laminins 8-11, and Cloning of a Novel α3 Isoform," Journal of Cell Biol, May 5, 1997, 137(3):685-701.

Nomizu, M. et al., "Identification of Cell Binding Sites in the Laminin α1 Chain Carboxyl-terminal Globular Domain by Systematic Screening of Synthetic Peptides," Journal of Biol Chem, Sep. 1, 1995, 270(35):20583-20590.

Nomizu, M. et al., "Identification of cell binding sequences in mouse laminin γ-1 chain by systematic peptide screening," Journal of Biol Chem, 1997, 272:32198-32205.

Nomizu, M. et al., "Cell Binding Sequences in Mouse Laminin α1 chain," J Biol Chem, Dec. 4, 1998, 273(46):32491-32499.

Nomizu, M. et al., "Identification of Homologous Biologically Active Sites on the N-Terminal Domain of Laminin Alpha Chains," Biochemistry, No month available, 2001, 40(50):15310-15317.

O'Reilly, M. et al., "Angiostatin: A Novel Angiogenesis Inhibitor That Mediates The Suppression of Metastases By a Lewis Lung Carcinoma," Cell, Oct. 21, 1994, 79:315-328.

O'Reilly, M. et al., "Endostatin: An Endogenous Inhibitor Of Angiogenesis and Tumor Growth," Cell, Jan. 24, 1997, 24(88):277-285.

Pepper, M., "Role of Matrix Metalloproteinases and Plasminogen Activator-Plasmin Systems in Angiogenesis," Arterioscler Thromb Vasc Biol, no month available, 2001, 21:1104-1117.

Plendl, J., et al., "Isolation and characterization of endothelial cells from different organs of fetal pigs," Anat Embryol, no month available, 1996, 194:445-456.

Rattan, S. et al., "Protein Synthesis, Posttranslational Modifications, and Aging," Ann NY Acad Sci, no month available, 1992, 663:48-62.

Risau, W., "Mechanisms of angiogenesis," Nature (Lond.), Apr. 17, 1997, 386:671-674.

Seifter, S. et al., "Analysis for Protein Modifications and Nonprotein Cofactors," Meth Enzymol, no month available, 1990, 182:626-646.

"Treatment of Age-related Macular Degeneration With Photodynamic Therapy (TAP) Study Group. Photodynamic Therapy of Subfoveal Choroidal Neovascularization In Age-related Macular Degeneration With Verteporfin: One-Year Results of 2 Randomized Clinical Trials—TAP Report 1," Arch Ophthalmol, Oct. 1999, 117(10):1329-1345.

Taraboletti, G. et al., "The heparin binding 25 kDa fragment of thrombospondin-1 promotes angiogenesis and modulates gelatinase and TIMP-2 production in endothelial cells," The FASEB Journal express article 10.1096/fj.99-0931fje., Jul. 24, 2000, 27 pages.

Timpl, R. et al., "The Laminins," Matrix Biol, no month available, 1994, 14:275-281.

Tolsma, S. et al., "Peptides Derived from Two Separate Domains of The Matrix Protein Thrombospondin-1 Have Anti-Angiogenic Activity," J. Cell Biol, Jul. 1993, 122(2):497-511.

Votruba, M. et al., "Neovascular age-related macular degeneration: present and future treatment options," Eye, no month available, 2001, 15(Pt. 3):424-429.

Wang, H. et al., "Murine hepatic microvascular adhesion molecule expression is inducible and has a zonal distribution," Clin Exp Metastasis, no month available, 1999, 17:149-1 55.

Wilhelmi, M., et al., "Endothelial Anatomy of the Human Heart:Immunohistochemical Evaluation of Endothelial Differentiation," Thorac Cardiovasc Surg., no month available, 2002, 50:230-236.

Zheng, X. et al., "Administration of noncytolytic IL-10/Fc in murine models of lipopolysaccharide-induced septic shock and allogeneic islet transplantation," Journal of Immunol, no month available, 1995, 154:5590-5600.

```
                         SEQUENCE LISTING

<160> NUMBER OF SEQ ID NOS: 13

<210> SEQ ID NO 1
<211> LENGTH: 12
<212> TYPE: PRT
<213> ORGANISM: Artificial
<220> FEATURE:
<223> OTHER INFORMATION: Scrambled version of C16 peptide
<300> PUBLICATION INFORMATION:
<301> AUTHORS: Ponce, M.L., Hibino, S., Lebioda, A.M., Mochizuki, M.,
      Nomizu, M., Kleinman, H.K.
<302> TITLE: Identification of a potent peptide antagonist to an active
      laminin-1 sequence that blocks angiogenesis and tumor growth
<303> JOURNAL: Cancer Research
<304> VOLUME: 63
<306> PAGES: 5060-5064
<307> DATE: 2003-08-15
<313> RELEVANT RESIDUES: (1)..(12)

<400> SEQUENCE: 1

Asp Phe Lys Leu Phe Ala Val Tyr Ile Lys Tyr Arg
1               5                   10

<210> SEQ ID NO 2
<211> LENGTH: 8
<212> TYPE: PRT
<213> ORGANISM: Artificial
<220> FEATURE:
<223> OTHER INFORMATION: Minimum active sequence of C16Y peptide
<300> PUBLICATION INFORMATION:
<301> AUTHORS: Ponce, M.L., Hibino, S., Lebioda, A.M., Mochizuki, M.,
      Nomizu, M., Kleinman, H.K.
<302> TITLE: Identification of a potent peptide antagonist to an active
      laminin-1 sequence that blocks angiogenesis and tumor growth
```

```
<303> JOURNAL: Cancer Research
<304> VOLUME: 63
<306> PAGES: 5060-5064
<307> DATE: 2003-08-15
<313> RELEVANT RESIDUES: (1)..(8)

<400> SEQUENCE: 2

Asp Phe Lys Leu Phe Ala Val Tyr
1               5

<210> SEQ ID NO 3
<211> LENGTH: 9
<212> TYPE: PRT
<213> ORGANISM: Artificial
<220> FEATURE:
<223> OTHER INFORMATION: 9 AA active fragment of C16Y peptide

<400> SEQUENCE: 3

Asp Phe Lys Leu Phe Ala Val Tyr Ile
1               5

<210> SEQ ID NO 4
<211> LENGTH: 10
<212> TYPE: PRT
<213> ORGANISM: Artificial
<220> FEATURE:
<223> OTHER INFORMATION: 10 AA active fragment of C16Y peptide

<400> SEQUENCE: 4

Asp Phe Lys Leu Phe Ala Val Tyr Ile Lys
1               5                   10

<210> SEQ ID NO 5
<211> LENGTH: 11
<212> TYPE: PRT
<213> ORGANISM: Artificial
<220> FEATURE:
<223> OTHER INFORMATION: 11 AA active fragment of C16Y peptide

<400> SEQUENCE: 5

Asp Phe Lys Leu Phe Ala Val Tyr Ile Lys Tyr
1               5                   10

<210> SEQ ID NO 6
<211> LENGTH: 10
<212> TYPE: PRT
<213> ORGANISM: Caenorhabditis elegans
<300> PUBLICATION INFORMATION:
<301> AUTHORS: C-elegans consortium
<302> TITLE: Genome sequence of the nematode c. elegans: a platform for
       investigating biology
<303> JOURNAL: Science (Wash. DC)
<304> VOLUME: 282
<306> PAGES: 2012-2018
<307> DATE: 1998
<313> RELEVANT RESIDUES: (1)..(10)

<400> SEQUENCE: 6

Asp Tyr Lys Tyr Phe Ala Val Tyr Tyr Arg
1               5                   10

<210> SEQ ID NO 7
<211> LENGTH: 4
<212> TYPE: PRT
<213> ORGANISM: Mus musculus
<300> PUBLICATION INFORMATION:
<301> AUTHORS: Nomizu, M., Yokoyama, F., Suzuki, N., Okazaki, I., Nishi,
       N., Ponce, L.P., Kleinman, H.K., Yamamoto, Y., Nakagawa, S.,
       Mayumi, T.
<302> TITLE: Identification of homologous biologically active sites on
```

```
               the N-terminal domain of laminin a chains
<303> JOURNAL: Biochemistry
<304> VOLUME: 40
<306> PAGES: 15310-15317
<307> DATE: 2001
<313> RELEVANT RESIDUES: (1)..(4)

<400> SEQUENCE: 7

Val Ala Tyr Ile
1

<210> SEQ ID NO 8
<211> LENGTH: 4
<212> TYPE: PRT
<213> ORGANISM: Mus musculus
<300> PUBLICATION INFORMATION:
<301> AUTHORS: Nomizu, M., Kuratomi, Y., Song, S.Y., Ponce, M.L.,
       Hoffman, M.P., Powell, S.K., Miyoshi, K., Otaka, A., Kleinman,
       H.K., Yamada, Y.
<302> TITLE: Identification of cell binding sequences in mouse laminin
       y-1 chain by systematic peptide screening
<303> JOURNAL: Journal of Biological Chemistry
<304> VOLUME: 272
<306> PAGES: 32198-32205
<307> DATE: 1997
<313> RELEVANT RESIDUES: (1)..(4)

<400> SEQUENCE: 8

Tyr Val Arg Leu
1

<210> SEQ ID NO 9
<211> LENGTH: 5
<212> TYPE: PRT
<213> ORGANISM: Mus musculus
<300> PUBLICATION INFORMATION:
<301> AUTHORS: Grant, D.S., Tashiro, K., Segui-Real, B., Yamada, Y.,
       Martin, G.R., Kleinman, H.K.
<302> TITLE: Two different laminin domains mediate the differentiation
       of human endothelial cells into capillary-like structures in vitro
<303> JOURNAL: Cell
<304> VOLUME: 58
<306> PAGES: 933-943
<307> DATE: 1989
<313> RELEVANT RESIDUES: (1)..(5)
<300> PUBLICATION INFORMATION:
<301> AUTHORS: Iwamoto, Y., Robey, F.A., Graf, J., Sasaki, M., Kleinman,
       H.K., Yamada, Y., Martin, G.R.
<302> TITLE: YIGSR a pentapeptide from the B1 chain of laminin inhibits
       tumor cell metastases
<303> JOURNAL: Science (Wash. DC)
<304> VOLUME: 238
<306> PAGES: 1132-1134
<307> DATE: 1987
<313> RELEVANT RESIDUES: (1)..(5)

<400> SEQUENCE: 9

Tyr Ile Gly Ser Arg
1               5

<210> SEQ ID NO 10
<211> LENGTH: 12
<212> TYPE: PRT
<213> ORGANISM: Artificial
<220> FEATURE:
<223> OTHER INFORMATION: Scrambled version of C16 peptide
<300> PUBLICATION INFORMATION:
<301> AUTHORS: Ponce, M.L., Nomizu, M., Kleinman, H.K.
<302> TITLE: An angiogenic laminin site and its antagonist bind through
       the avB3 and a5B1 integrins
<303> JOURNAL: FASEB J
<304> VOLUME: 15
<306> PAGES: 1389-1397
<307> DATE: 2001-06
```

```
<313> RELEVANT RESIDUES: (1)..(12)

<400> SEQUENCE: 10

Lys Ala Phe Asp Ile Thr Tyr Val Arg Leu Lys Phe
1               5                   10

<210> SEQ ID NO 11
<211> LENGTH: 12
<212> TYPE: PRT
<213> ORGANISM: Artificial
<220> FEATURE:
<223> OTHER INFORMATION: Scrambled version of C16 peptide
<300> PUBLICATION INFORMATION:
<301> AUTHORS: Ponce, M.L., Hibino, S., Lebioda, A.M., Mochizuki, M.,
       Nomizu, M., Kleinman, H.K.
<302> TITLE: Identification of a potent peptide antagonist to an active
       laminin-1 sequence that blocks angiogenesis and tumor growth
<303> JOURNAL: Cancer Research
<304> VOLUME: 63
<306> PAGES: 5060-5064
<307> DATE: 2003-08-15
<313> RELEVANT RESIDUES: (1)..(12)

<400> SEQUENCE: 11

Ile Lys Asp Tyr Leu Thr Phe Ala Arg Val Lys Phe
1               5                   10

<210> SEQ ID NO 12
<211> LENGTH: 12
<212> TYPE: PRT
<213> ORGANISM: Artificial
<220> FEATURE:
<223> OTHER INFORMATION: Scrambled version of C16 peptide
<300> PUBLICATION INFORMATION:
<301> AUTHORS: Ponce, M.L., Hibino, S., Lebioda, A.M., Mochizuki, M.,
       Nomizu, M., Kleinman, H.K.
<302> TITLE: Identification of a potent peptide antagonist to an active
       laminin-1 sequence that blocks angiogenesis and tumor growth
<303> JOURNAL: Cancer Research
<304> VOLUME: 63
<306> PAGES: 5060-5064
<307> DATE: 2003-08-15
<313> RELEVANT RESIDUES: (1)..(12)

<400> SEQUENCE: 12

Leu Thr Phe Arg Ala Lys Val Tyr Phe Ile Lys Asp
1               5                   10

<210> SEQ ID NO 13
<211> LENGTH: 12
<212> TYPE: PRT
<213> ORGANISM: Mus musculus

<400> SEQUENCE: 13

Lys Ala Phe Asp Ile Thr Tyr Val Arg Leu Lys Phe
1               5                   10
```

THERAPEUTIC ADMINISTRATION OF THE SCRAMBLED ANTI-ANGIOGENIC PEPTIDE C16Y

FIELD OF THE INVENTION

The present invention relates to the field of ocular disease, in particular diseases associated with ocular neovascularization, and to the field of cancer therapy, specifically breast cancer therapy. In addition, the present invention relates to angiogenesis, angiogenesis inhibitors, integrins, and integrin pathway inhibition.

BACKGROUND

The extracellular matrix (ECM), often referred to as connective tissue, is the complex structure that surrounds and supports cells in mammalian tissue. It is composed primarily of three classes of biomolecules: structural proteins (collagen and elastin), specialized proteins (e.g., laminin, fibronectin, fibrillin), and proteoglycans (core proteins linked to repeating disaccharides known as glycosaminoglycans or GAGs) (Pepper 2001). The ECM is vital for the maintenance and differentiation of many cell types, including the endothelium. In addition, it plays a role in the formation of new blood vessels from pre-existing ones, a process known as angiogenesis (Folkman 1995; Risau 1997).

Most normal cells cannot survive unless anchored to the ECM. This anchoring is mediated by heterodimeric transmembrane glycoproteins called integrins, which act as cellular adhesion receptors. Integrins are composed of non-covalently associated α and β subunits. Sixteen α subunits and eight β subunits have been identified, and over 20 different combinations of these subunits have been found. For example, integrin αvβ3 is a receptor on the surface of endothelial cells in growing blood vessels. It binds angiogenic endothelial cells, enabling them to form new blood vessels. Integrins anchor cells to their surroundings by mediating cell-matrix and cell-cell interactions. The extracellular portion of the integrin binds to collagen, laminin, or fibronectin, while the intracellular portion binds to actin filaments or the cytoskeleton. Extracellular binding to matrix proteins is dependent in large part on recognition of an RGD motif in the extracellular proteins. Fibronectin is the prototype RGD-containing protein.

Angiogenesis is the formation of new blood vessels from preexisting ones. Under normal conditions, angiogenesis is subject to tight physiological regulation, and the proliferation of endothelial cells is very low. Increased angiogenesis normally occurs in wound healing, embryonic development, and the monthly growth of the uterine lining in menstruating females. However, there are other situations in which increased angiogenesis is associated with a pathological condition. Uncontrolled angiogenesis has been associated with tumor growth, tumor metastasis, diabetic retinopathy, rheumatoid arthritis, and cardiovascular disease (Folkman 1995).

The endothelial cells that make up blood vessels generally remain in a quiescent state until they receive an angiogenic signal from their microenvironment. These signals may be triggered by wounds, inflammation, or disease. The angiogenic signal activates the endothelium and elicits a cascade of events that leads to new vessel formation: induction of proteases, degradation of the basement membrane, migration of endothelial cells into interstitial space, endothelial cell proliferation, lumen formation, generation of new basement membrane, fusion of new vessels, and initiation of blood flow.

The first step in the angiogenic cascade is the release of proteases such as matrix metalloproteinases (MMPs) by endothelial cells. These proteases degrade the basement membrane, a specialized type of ECM. The basement membrane is a storage depot for many angiogenic growth factors, such as vascular endothelial growth factor (VEGF) and basic fibroblast growth factor (bFGF). Degradation of the basement membrane releases these angiogenic growth factors, which in turn propagates the angiogenic cascade. Degradation of the ECM also results in the release of ECM protein fragments, several of which have been implicated in the modulation of angiogenesis. Some of these fragments (e.g., an Mr 25,000 thrombospondin fragment) promote angiogenesis, while other fragments (e.g., endostatin derived from collagen XVIII, angiostatin derived from plasminogen, the noncollagenous domains of collagen IV, and several thrombospondin peptides) inhibit it (Taraboletti 2000; O'Reilly 1997; O'Reilly 1994; Maeshima 2001; Tolsma 1993).

Endothelial cells in blood vessels are in contact with a basement membrane that contains laminin, a large ubiquitous glycoprotein that exists in twelve different isoforms. Laminin is composed of three chains (α, β, and γ). Five different α, three β, and three γ chains have been identified. Ten of the twelve different heterotrimeric isoforms contain the γ1 chain (Timpl 1994; Burgeson 1994; Miner 1997). The identity of the laminin isoforms present in the endothelial cell matrix has not been determined. However, polyclonal antibodies to laminin-1 (composed of α1, β1, and γ1) recognize the matrix, suggesting the presence of at least one of these three chains. Laminin-1 promotes the attachment of endothelial cells in vivo, and the cells differentiate into capillary-like structures when plated on a laminin-1-rich basement membrane, such as Matrigel (Kubota 1988). Multiple binding sites for tumor cells have been identified on laminin-1 (Nomizu 1995; Nomizu 1997; Nomizu 1998).

More than twenty peptides from laminin-1 have been identified that can promote angiogenesis in vivo (Malinda 1999; Ponce 1999). These include eight peptides from the α1 chain, five from the β1 chain, and seven from the γ1 chain. Two of the most potent angiogenic peptide sites, A13 and C16, are redundant angiogenic sites present in homologous regions of the α1 and γ1 chains, respectively (Ponce 2003a; Kuratomi 2002; Kuratomi 1999). These peptide sequences bind to the endothelial cell integrins αvβ3 and α5β1, and have been shown to promote adhesion, tube formation, and angiogenesis in the chick chorioallantoic membrane (CAM) assay (Ponce 2001). The mechanism of action of these peptides has not yet been identified. Although they bind to integrins, they do not seem to signal through mitogen-activated protein kinase or several serine or threonine kinases. Eleven of the thirteen laminin proteins contain γ1 chains, meaning that the C16 sequence is present in eleven laminins (Colognato 2001). In addition, the A13 sequence is highly conserved in the laminin α chains. This means that several of the laminins, including laminin-1 and laminin-3, contain the A13 sequence twice (Nomizu 2001).

Because of the putative significance of the C16 sequence in angiogenesis and its related diseases, it has been important to identify antagonists capable of blocking its activity. One such antagonist is the scrambled peptide sequence C16S, which has been shown to inhibit C16 and bFGF-induced angiogenesis in the CAM assay (Ponce 2001). The methods disclosed in the present invention utilize a modified C16 peptide sequence, C16Y, which is at least five times more potent than C16S. C16Y inhibits choroidal neovascularization (CN) in vivo, in addition to inhibiting in vivo angiogenesis and tumor growth in mice (Ponce 2003b). Based on determination of its minimum active sequence, C16Y has been shown to share homology with fibronectin.

Unregulated angiogenesis is associated with the change of tumors from a quiescent state to a malignant state. Tumors require an extensive capillary network to grow and metastasize. Normally, a solid tumor will not grow beyond approximately 2 mm without the development of new blood vessels. Pathological or unregulated angiogenesis in the eye (ocular neovascularization) is the most common cause of blindness, and has been implicated in roughly twenty different eye diseases. The primary types of ocular neovascularization are retinal neovascularization, choroidal neovascularization, corneal neovascularization, and iris neovascularization.

Retinal neovascularization is the development of new blood vessels originating from the retinal veins and growing into the vitreous. Retinal neovascularization is associated with diabetic retinopathy, retinopathy of prematurity, central vein occlusion, and other retinal diseases. Diabetic retinopathy is responsible for 13-18% of newly reported cases of blindness (Kohner 1975), and it is the leading cause of legal blindness in people under 65 years old. Choroidal neovascularization (CN) is the development of new blood vessels in the vascular choroid, an area made up of large choroidal vessels and the choriocapillaris. The choriocapillaris is located next to the retinal pigmented epithelium and Bruch's membrane, and provides vascular support to the outer retina. CN is associated with a variety of diseases, including age-related macular degeneration (AMD) and high myopia. AMD is the leading cause of irreversible vision loss in world for people over 50 years old (Votruba 2001). Iris neovascularization, or rubeosis, often leads to the development of neovascular glaucoma. Corneal neovascularization, often associated with the use of contact lenses, can lead to vision loss.

SUMMARY OF THE INVENTION

Angiogenesis plays a key role in several pathological conditions, including cancer and ocular neovascularization. Tumors are unable to grow and metastasize without the formation of new blood vessels. Angiogenesis in the eye (ocular neovascularization) is associated with a variety of ocular diseases, including age-related macular degeneration (AMD) and diabetic retinopathy. The present invention discloses peptides that inhibit angiogenesis, and methods of utilizing these peptides to treat conditions associated with angiogenesis. Specifically, the present invention discloses the scrambled C16 peptide, C16Y, and methods of utilizing this peptide to treat cancer and conditions associated with ocular neovascularization.

In a first aspect, the present invention provides a method for treating a condition associated with ocular neovascularization by administering a peptide comprising the full-length C16Y peptide sequence of SEQ ID NO: 1, or a fragment of the C16Y peptide as set forth in SEQ ID NO: 2, SEQ ID NO: 3, SEQ ID NO: 4, or SEQ ID NO: 5. In a preferred embodiment, the condition is associated with choroidal neovascularization, preferably age-related macular degeneration or high myopia. In another preferred embodiment, the condition is associated with retinal neovascularization, preferably diabetic retinopathy, retinopathy of prematurity, or central vein occlusion. In another preferred embodiment, the condition is associated with iris neovascularization, preferably neovascular glaucoma. In certain preferred embodiments, the method utilizes a peptide that has undergone various modifications to enhance its pharmacodynamic characteristics.

In a second aspect, the present invention provides a method for treating cancer in a subject by administering a peptide comprising the full-length C16Y peptide sequence of SEQ ID NO: 1, or a fragment of the C16Y peptide as set forth in SEQ ID NO: 2, SEQ ID NO: 3, SEQ ID NO: 4, or SEQ ID NO: 5. In a preferred embodiment, the cancer being treated is breast cancer. In certain preferred embodiments, the method utilizes a peptide that has undergone various modifications to enhance its pharmacodynamic characteristics.

In a third aspect, the present invention provides a pharmaceutical composition in which a peptide comprising the full-length C16Y peptide sequence of SEQ ID NO: 1 or a fragment of the C16Y peptide as set forth in SEQ ID NO: 2, SEQ ID NO: 3, SEQ ID NO: 4, or SEQ ID NO: 5 is the active component. In preferred embodiments, the peptides have undergone certain modifications to enhance their pharmacodynamic characteristics.

In a fourth aspect, the present invention provides a kit for the treatment of a condition associated with ocular neovascularization, wherein the primary component of the kit is either a peptide comprising the full-length C16Y peptide sequence of SEQ ID NO: 1 or a fragment of the C16Y peptide as set forth in SEQ ID NO: 2, SEQ ID NO: 3, SEQ ID NO: 4, or SEQ ID NO: 5.

DETAILED DESCRIPTION

Figure 1:
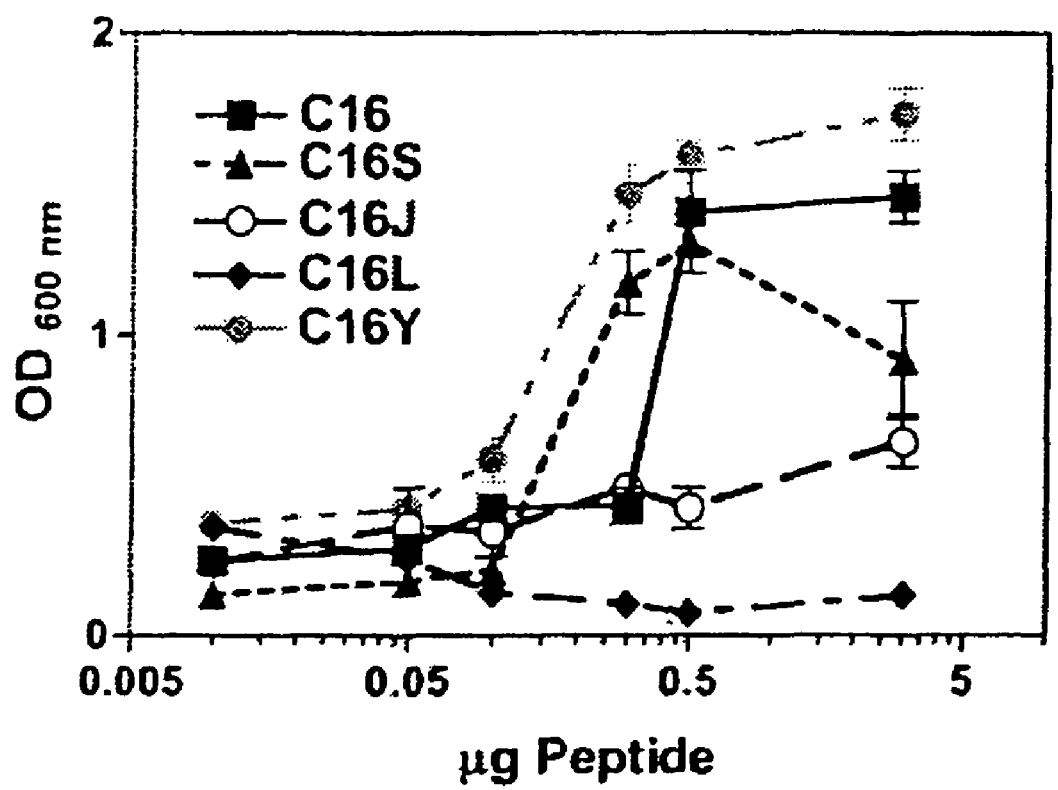
FIG. 1: Endothelial cell adhesion by C16 and scrambled C16 peptides. 96-well plates were coated with either laminin-1 (0.5 µg), C16 peptide (0-5 µg), or scrambled C16 peptide (0-5 µg). Each well was rinsed with PBS, blocked with BSA, rinsed again with PBS, and then treated with 0.1 ml of RPMI containing 35,000 human umbilical vein endothelial cells (HUVECs) for 1.5 hours at 37° C. Unbound cells were decanted, and attached cells were stained with crystal violet and quantified by measuring their absorbance at 600 nm. Cells adhered to C16, C16S, and C16Y peptides. More cells adhered to C16Y than to any other peptide at all concentrations tested. Bars represent ±SD.

A variety of therapies have been previously employed or suggested to treat ocular neovascularization. For instance, choroidal and retinal neovascularization have both been treated using a technique called laser photocoagulation, which coagulates the blood vessels and prevents them from spreading. However, this technique does nothing to prevent the recurrence of neovascularization, and can leave the patient with a blind spot arising from scarring. CN has been treated by surgically removing the choroidal neovascular complex, but this procedure is very hazardous and is also associated with vision loss. Photodynamic therapy, which is essentially a more precise version of laser photocoagulation, has been employed to treat CN. In this procedure, a light sensitive dye such as verteporfin accumulates in areas of neovascularization, providing a target for laser-induced coagulation (TAP Study Group 1999). Other treatment options include exposure to low level radiation, which may prevent new vessel formation, and cryotherapy (i.e., freezing), which may shrink abnormal blood vessels.

As an alternative to the above therapeutic methods, anti-angiogenic compounds may be employed. Anti-angiogenic compounds may be used to treat any condition associated with angiogenesis, including ocular neovascularization, cancer, and arthritis. A variety of anti-angiogenic compounds have been utilized or suggested for the treatment of conditions associated with angiogenesis. For example, U.S. Pat. No. 5,932,545 discloses the use of short peptide sequences derived from the stalk region of thrombospondin-1. U.S. Pat. No. 6,028,099 discloses the use of genistein, a protein tyrosine kinase pathway inhibitor. U.S. Pat. No. 6,444,680 discloses the administration of the amine salts of an integrin receptor antagonist to treat AMD. U.S. Pat. No. 6,524,581 discloses administration of an antibody that inhibits leukocyte adhesion to treat diabetic retinopathy. U.S. Pat. No. 6,670,321 suggests the use of various integrin antagonists in conjunction with compounds that prevent leukocyte adhesion to treat diabetic retinopathy. U.S. Pat. No. 6,509,347 describes the use of an integrin antagonist comprising crystalline propionic acid. Vascular endothelial growth factor (VEGF), the most well understood ocular angiogenesis mediator, has been a common target for anti-angiogenic CN therapies. Antibodies and oligonucleotides that bind VEGF have been employed, along with compounds that block the downstream effects of VEGF (Ciulla 2003). Other anti-angiogenic compounds employed to treat conditions associated with angiogenesis include melanin or melanin promoters (U.S. Pat. No. 6,525,019), prostaglandin derivatives (U.S. Pat. No. 6,225,348), phytoestrogenic isoflavone (U.S. Pat. No. 6,001,368), angiotensin converting enzyme inhibitors (U.S. Pat. No. 4,656,188), cyclic peptides (U.S. Pat. Nos. 5,767,071, 5,780,426, 5,821,329, and 6,096,707), and a variety of steroid compounds (Ciulla 2003).

The term "peptide" as used herein refers to two or more amino acids linked together via a peptide bond. The amino acids making up a peptide may be any of the 20 standard genetically-encoded amino acids, other naturally occurring amino acids, unnatural amino acids, or chemically derivatized amino acids, and may exist as L form isomers or D form isomers. In addition, the term "peptide" may refer to peptide mimetics or peptides that have undergone a variety of chemical modifications. The present invention utilizes standard notation for peptide sequences, wherein the left end of the molecule is the amino terminal end and the right end is the carboxy terminal end.

The term "ocular neovascularization" as used herein refers to any pathological, abnormal, or unregulated angiogenesis in any of the components of the eye. The term may refer to choroidal, retinal, corneal, or iris neovascularization, or any other type of abnormal vessel growth in the eye.

A "condition associated with ocular neovascularization" as used herein refers to any condition which exhibits ocular neovascularization as a symptom, or any condition that is caused by ocular neovascularization. Such conditions include but are not limited to age-related macular degeneration, diabetic retinopathy, neovascular glaucoma, high myopia, retinopathy of prematurity, central vein occlusion, branch retinal vein occlusion, presumed ocular histoplasmosis, angioid streaks, and partial or total vision loss.

The term "cancer" as used herein refers to a condition marked by solid tumor formation, wherein the solid tumor requires the development of new blood vessels in order to grow and metastasize. "Cancer" as used herein does not encompass a condition marked by dispersed cancer or non-solid tumor formation, such as leukemia or lymphoma. A "solid tumor" is a tumor-formed by abnormal and uncontrolled cell growth in any body tissue other than blood, lymphatic system, or bone marrow. Examples of solid tumors include tumors of the breast, colon, or prostate.

The term "subject" as used herein refers to any animal, but preferably refers to a mammal or more preferably to a human.

The term "treating" as used herein means preventing, eliminating, or slowing the advancement of a condition. The term also encompasses eliminating or reducing a symptom or symptoms associated with a condition, and delaying or preventing an increase in these symptoms.

A "composition" as used herein refers to the active agent, i.e., the peptide or peptides of the present invention, alone or in combination with one or more compounds or compositions. A "pharmaceutical composition" as used herein refers to the active agent combined with one or more pharmaceutically acceptable diluents, preservatives, solubilizers, emulsifiers, adjuvants, stabilizers, and/or carriers, making the composition suitable for therapeutic administration.

The peptides of the present invention are scrambled versions of the C16 peptide, the most active peptide sequence from the γ1 chain of laminin-1 (Ponce 1999; Ponce 2003a; Kuratomi 2002). Laminin-1 is biologically active basement membrane-derived glycoprotein that acts to increase cell adhesion, cell migration, cell differentiation, tumor growth, and angiogenesis via multiple active sites (Pupa 2002). Many cellular receptors to laminin-1 have been identified (Powell 1997). For instance, the active site contained in C16 binds to integrins α5β1 and αvβ3. A scrambled version of the C16 peptide, C16S, was created as a negative control, but had unexpected antagonist activity (Ponce 2001). The scrambled C16S peptide bound to the integrin receptors and promoted cell adhesion, but prevented the cell from binding to the parent C16 peptide and to laminin-1. C16S also blocked peptide- and fibroblast growth factor-mediated angiogenesis in the chick CAM assay.

A variety of amino acid substitutions were performed using the sequence of C16S, with the goal of developing more potent C16 antagonists. Five scrambled peptides (C16S, C16J, C16L, C16-3, and C16Y) were created and tested for their ability to inhibit angiogenesis.

Endothelial cell adhesion assays were performed using plates coated with either laminin or one of the scrambled C16 peptides. Endothelial cells did not attach to C16L, and attached only weakly to C16J. The cells adhered to C16Y, C16, and C16S, with more cells adhering to C16Y than to the other two peptides.

The peptides were next tested for their ability to block adhesion of endothelial cells to laminin-1. Plates were coated with laminin-1 in the presence of various concentrations of peptides. C16J had little inhibitory activity, and C16L had inhibitory activity only at higher concentrations. The best inhibitors were C16Y, C16, and C16S, with C16Y displaying substantially higher inhibitory activity than the other two.

Endothelial tube-forming assays were performed in Matrigel in the presence of various peptide concentrations. It had been shown previously that C16, which is angiogenic, and C16S, its antagonist, were both active in the endothelial cell tube formation assay at doses greater than 50 µg/ml (Ponce 2001). C16J, C16-3, and C16L displayed little ability to inhibit endothelial cell tube formation. C16Y, C16, and C16S, on the other hand, all inhibited tube formation. C16Y was the best inhibitor by a substantial margin, with the ability to inhibit tube formation at concentrations five times lower than C16 or C16S. Truncated versions of C16Y were tested to determine the minimal active sequence of the peptide. The minimal active sequence was an eight amino acid sequence from the amino terminal end of the peptide. Every peptide containing this minimal active sequence disrupted tube formation. The carboxyl end of the peptide was not necessary for activity.

Results of the endothelial cell adhesion and competition assays suggested that C16Y promotes cell attachment, and that it competes more strongly with laminin-1 for binding than any of the other scrambled peptides, including C16S. In addition, C16Y actively disrupts endothelial cell tube formation. These traits are highly suggestive of a compound that either inhibits or promotes angiogenesis (Ponce 1999, Ponce 2003a).

The ability of C16Y peptide to inhibit angiogenesis was tested using the CAM assay. C16 peptide was administered as an angiogenic stimulus in the presence of varying concentrations of scrambled peptides. C16 administered alone induced substantial angiogenesis in the CAM. Co-administration of C16Y or C16S markedly decreased this angiogenic effect. At higher concentrations, the level of inhibition by C16Y was roughly 25% greater than that of C16S. At lower concentrations, C16S lost its inhibitory ability, while C16Y continued to substantially inhibit angiogenesis.

The ability of the C16Y peptide to inhibit tumor growth in vivo was tested using CAMs treated with breast tumor cells. Administration of the angiogenic peptide C16 did not considerably affect tumor growth. At all concentrations tested, C16Y inhibited tumor growth by approximately 40%. To determine whether this antitumor effect was due to angiogenesis inhibition or due to a decrease in cell proliferation, the effect of C16Y on cell proliferation was measured. C16Y was incapable of altering tumor cell proliferation, suggesting that its ability to inhibit tumor growth derives from its ability to inhibit angiogenesis.

Further experiments to examine the ability of C16Y to inhibit tumor growth in vivo were performed on mice that had been subcutaneously injected with breast cancer cells. Varying concentrations of C16Y were administered daily by intraperitoneal injection after tumors were established. After one week, tumors treated with C16Y displayed substantially less growth than those treated with control or with C16. When administration of C16Y was halted after one week, tumors began to grow rapidly. This tumor growth was greatest in those mice that received the lowest dosages of C16Y.

The ability of C16Y to inhibit CN in vivo was tested using C57/BL6 mice that had been subjected to multiple laser-induced choroidal lesions in the area adjacent to the optical nerve. Mice were treated daily with C16Y, a control peptide, or water by intraperitoneal injection for 14 days. Mice were sacrificed, and their eyes were perfused and prepared for examination. Choroids were examined by microscopy, and the area of each neovascular lesion was quantitated. Mice treated with C16Y displayed a substantial decrease in lesion area compared to control mice.

These results suggest that C16Y has tremendous therapeutic potential as a means of treating conditions associated with angiogenesis. Specifically, C16Y has shown the ability to inhibit breast tumor growth and ocular neovascularization. The ability of C16Y to inhibit angiogenesis is 5-10 fold greater than that of C16S, the other scrambled C16 peptide that displays anti-angiogenic activity. These results would not have been predicted, since the only difference between the two peptides is a single threonine to tyrosine substitution. C16Y is active in vivo, and can inhibit tumor growth in a dose-dependent manner when given daily as an i.p. injection. C16Y likely exerts its influence on tumor growth by blocking angiogenesis, because it has no effect on tumor cell proliferation in vitro.

C16Y is not toxic but may interfere with the normal functions of laminin-1, as well as other molecules that use the integrin $\alpha 5 \beta 1$ and $\alpha v \beta 3$ receptors. Angiogenesis has been shown to require the activity of integrin $\alpha v \beta 3$ (Friedlander 1995; Brooks 1994). Laminin-1 has many biological activities that would promote tumor growth and angiogenesis (Kleinman 2001). Laminin-1 promotes cell adhesion, migration, invasion, and protease activity, and laminin-1-adherent cells are more malignant than nonadherent cells or fibronectin-adherent cells. Because several laminin-1 peptides can modulate tumor growth and angiogenesis in vivo, endogenous laminin-1 is likely physiologically active in vivo during tumor growth and angiogenesis, although this has not yet been demonstrated directly in vivo. The C16 site on laminin-1 appears to be functionally important in vivo in both tumor growth and angiogenesis, and that this active site on laminin-1 is blocked by the C16Y peptide. In previous screens to identify active sites for malignancy on laminin-1, C16 and its homologue on the $\alpha$ chain, A13, were identified as being the most potent on their respective chains (Malinda 1999; Ponce 1999; Kuratomi 1999; Nomizu 2001; Nomizu 1997). Furthermore, either or both of these redundant active sites are present in all of the laminin-1 isoforms. When initially preparing control peptides for C16, many different randomly scrambled peptides were prepared. Most were inactive, but some had low activity, and C16S had the highest activity (Kuratomi 2002). A comparison study of the full-length C16Y sequence (SEQ ID NO: 1) was made to identify amino acid homology to other short sequences using National Center for Biotechnology Information Protein BLAST search. These results indicate that C16Y shares 66% (8 of 12) identity to the fibronectin sequence (residues 1023-1033) of c-elegans, the sequence of which is shown in SEQ ID NO: 6 (C-elegans consortium 1998). However, a peptide having this sequence demonstrated no ability to block endothelial tube formation (results not shown), further illustrating the unexpectedness of C16Y's anti-angiogenic activity.

It had already been established that VAYI (SEQ ID NO: 7) was the minimal active sequence for A13 and that this sequence is highly conserved among the $\alpha$ chains (Nomizu 2001). With C16, the minimal active sequence was found previously to be YVRL (SEQ ID NO: 8) (Nomizu 1997). Although different in sequence, these peptides are located in homologous sites on laminin-1 and recognize the same cellular receptors. The minimal active sequence of C16Y is the eight amino acid sequence of SEQ ID NO: 2. Each of the peptides containing this minimal active sequence (SEQ ID NOs: 1-5) displayed anti-angiogenic activity. All of these peptides regulate angiogenesis and recognize the promiscuous integrin $\alpha v \beta 3$ (Varner 1996; Sakamoto 1991). Many sites for angiogenesis have been identified on laminin-1, but only one site has been found to be an inhibitor of angiogenesis, YIGSR (SEQ ID NO: 9), which is located on the $\beta 1$ chain (residues 929-933; Grant 1989; Iwamoto 1987). This peptide also blocks tumor growth and lung colonization but is much less active (~10-fold) than the C16Y peptide described here (Fridman 1990). C16Y is the most potent peptide described to date and may function as an antagonist to integrins during angiogenesis.

The pharmaceutical compositions of the present invention include effective amounts of peptides comprising the sequences of SEQ ID NO: 1, SEQ ID NO: 2, SEQ ID NO: 3, SEQ ID NO: 4, or SEQ ID NO: 5, in conjunction with one or more pharmaceutically acceptable diluents, preservatives, solubilizers, emulsifiers, adjuvants, stabilizers, and/or carriers. One skilled in the art will be able to determine the effective amount of the peptides by administering the composition at various dosages and observing the results. The effective amount is that amount which generates the desired response within a reasonable time period, and may vary depending on the age, health, or size of the subject, or on the severity of the condition being treated. The desired response is inhibition of angiogenesis to treat a condition. This condition may be cancer, or it may be a condition associated with ocular neovascularization. Inhibition of angiogenesis may result in the prevention, slowing, or elimination of the condition, the reduction or elimination of symptoms associated with the condition, or the delay or prevention of a worsening of these symptoms.

The compositions of the present invention may be administered in single or multiple administrations, at constant dosages or at varying dosages to be determined by the practitioner. The composition of the present invention may be administered alone, or in conjunction with other therapeutic or non-therapeutic compounds. In addition, the composition may be administered in conjunction with any chemotherapeutic, surgical, photodynamic, or photocoagulation therapy. The preferred route of administration for the treatment of a condition associated with ocular neovascularization is intraocularly. However, the composition may also be administered by any other effective means, including but not limited to orally or by intraperitoneal, subcutaneous, intramuscular, or intravenous injection. The composition may be administered for therapeutic treatment in a subject exhibiting ocular neovascularization or cancer, or for prophylactic treatment in a subject that has not yet exhibited ocular neovascularization or cancer. The subject is preferably human, but may be any animal with cancer, or any animal that exhibits a condition associated with ocular neovascularization, including but limited to mammals such as dogs, cats, horses, or cattle.

One skilled in the art will recognize that the peptides of the present invention may undergo a variety of modifications without departing from the scope of the invention. Modifications may be incorporated that increase stability, circulation time, and therapeutic efficacy (see Francis 1992 for a review of peptide modifications). Potential modifications that may be performed on the peptides of the present invention include chemical modifications, which include but are not limited to pegylation, acylation, biotinylation, acetylation, formylation, ubiquitination, amidation, enzyme labeling, or radiolabeling. For instance, varying degrees of pegylation may be used to vary the half-life of the peptide, with increased pegylation corresponding to increased half-life. Each of these peptide modifications is well-known in the art. See, for example, Seifter 1990; Rattan 1992; Proteins—Structure and Molecular Properties, 2$^{nd}$ Ed., T. E. Creighton, W.H. Freeman and Company, New York, 1993; Wold, F., "Posttranslational Protein Modifications: Perspectives and Prospects", pgs. 1-12 in Posttranslational Covalent Modification of Proteins, B. C. Johnson, Ed., Academic Press, New York, 1983. Modifications may be occur at any location on the peptide, including the peptide backbone, the amino acid side chains, and the amino or carboxy termini. In another example, the peptides of the invention may be modified by addition of the Fc domain of an antibody. The Fc domain of an antibody is a relatively constant region that is responsible for biological activity rather than antigen binding. A variety of therapeutic polypeptides have been created using the Fc domain to increase the half-life of the polypeptide or to incorporate certain biological functions such as the ability to bind to a particular receptor (for example, U.S. Pat. No. 5,480,981; Harvill 1995; Zheng 1995; Fisher 1996). Attachment of an Fc domain to the peptides of the present invention is likely to increase the half-life of the peptides, which will in turn increase their therapeutic utility. The Fc domain may comprise portions of a digested, naturally occurring antibody, or it may be derived from a recombinant or humanized antibody.

The present invention also encompasses the use of peptide mimetics to the C16Y full-length and truncated peptides. Those skilled in the art will be familiar with a variety of techniques for generating peptide mimetics, for instance those techniques disclosed in U.S. Pat. Nos. 4,612,132; 5,643,873; and 5,654,276. Peptide mimetics may incorporate one or more of the following: modifications of the N-terminal amino group, modifications of the C-terminal carboxyl group, and changes in one or more of the peptide amino linkages to non-amino linkages. Peptide mimetics may include synthetic structures, but they retain the functional and structural characteristics of the parent peptide by maintaining the relative amino acid sequence and spatial positioning of the parent peptide. Peptide mimetics may possess a variety of therapeutic advantages over the parent peptide, including but not limited to increased solubility, increased stability and half-life, or decreased susceptibility to hydrolysis and proteolysis.

The method of the present invention also encompasses the use of different isomeric forms of the full-length and truncated C16Y peptides. The peptides of the present invention may consist entirely of L form or D form amino acids, or they may consist of some combination of D and L form amino acids. Methods for synthesizing peptides that contain one or more D form amino acids are well-known in the art. Peptides containing one or more D form amino acids are metabolized more slowly and are more resistant to proteolysis than their L form counterparts, primarily because humans lack the necessary endogenous enzymes to degrade. D form peptides (Fujihara 2000). The resultant increase in peptide stability and half-life is likely to increase the therapeutic efficacy of the claimed methods.

EXAMPLES

Materials and Methods

Peptides

All peptides were synthesized by the CBER Facility for Biotechnology Resources (Food and Drug Administration, Bethesda, Md.) or at Hokkaido University as described previously (Nomizu 2001), and each contained an NH$_2$-terminal amide. C16S (SEQ ID NO: 10), C16J (SEQ ID NO: 11), C16L (SEQ ID NO: 12), and C16-3 are scrambled peptides of C16 (SEQ ID NO: 13). C16Y (SEQ ID NO: 1) is identical to C16S except for one threonine to tyrosine substitution.

Various truncated peptides were prepared in similar fashion for determination of the minimal active sequence. Despite the presence of hydrophobic amino acids, all of the peptides were water-soluble. Laminin-1 was obtained from Collaborative Research (Bedford, Mass.).

Isolation and Culture of Endothelial Cells

Endothelial cells were isolated by collagenase treatment from human umbilical vein endothelial cells (HUVECs), and were cultured as described previously (Jaffe 1973). Only those cells from passages 3-5 were used.

Example 1

Endothelial Cell Adhesion by C16 and Scrambled C16 Peptides

Endothelial cell adhesion assays were performed on 96-well plates coated overnight with either laminin-1 (0.5 µg) or synthetic laminin peptides C16, C16S, C16J, C16L, or C16Y (0-5 µg) as described previously (Malinda 1999). Wells were rinsed with PBS, blocked with 2 mg/ml of BSA, and rinsed again with PBS. Cell adhesion was performed using 0.1 ml of RPMI 1640 containing 35,000 HUVECs. After a 1.5-hour incubation period at 37° C., unbound cells were decanted and attached cells were fixed and stained with 20% methanol/0.2% crystal violet. Dishes were extensively rinsed, and bound dye was solubilized in 2% SDS and quantitated at 600 nm. Assays were done in triplicate at least three times.

Cells attached to C16, the parent peptide, and to C16S at amounts >0.1 µg (FIG. 1). Although C16Y showed a similar attachment pattern to that of C16 and C16S, more cells adhered to it than to any other peptide at all of the amounts tested. Endothelial cells did not attach to C16L at any dose, and the cells only weakly bound to those wells coated with the highest amounts of C16J.

Example 2

Ability of C16 and Scrambled C16 Peptides to Block Laminin-1 Endothelial Cell Adhesion Competition experiments were done using 96-well plates coated with laminin-1 (0.5 µg) in the presence of 0-100 µg/ml of competing C16, C16S, C16J, C16L, or C16Y synthetic laminin peptide as specified. Control wells were coated with BSA only. Wells were contacted with 0.1 ml of RPMI 1640 containing 35,000 HUVECs. After a 1.5-hour incubation at 37° C., unbound cells were decanted and attached cells were fixed and stained with 20% methanol/0.2% crystal violet. Dishes were extensively rinsed, and bound dye was solubilized in 2% SDS and quantitated at 600 nm. Assays were done in triplicate at least three times.

Figure 2:
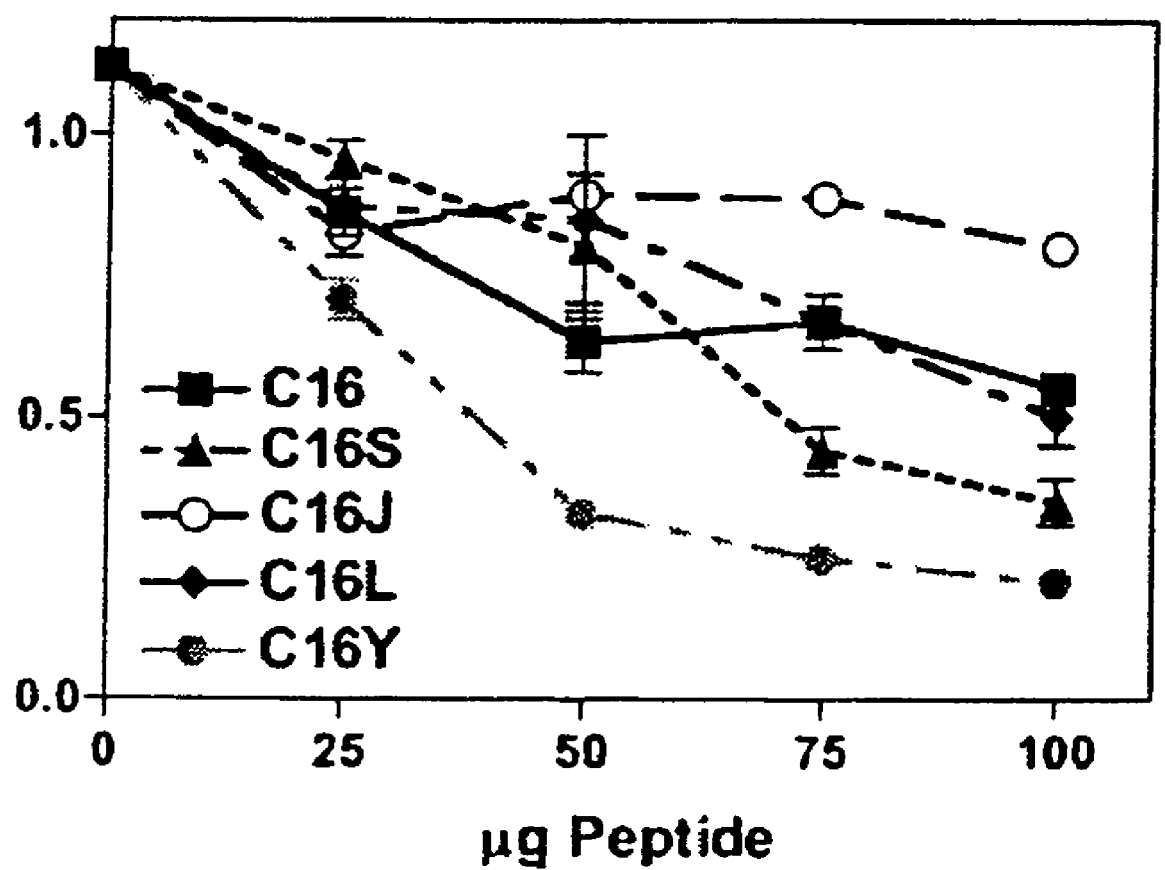
FIG. 2: Ability of C16 and scrambled C16 peptides to block laminin-1 endothelial cell adhesion. 96-well plates were coated with laminin-1 (0.5 µg) in the presence of competing C16 or scrambled C16 peptides (0-100 µg/ml). Each wells was treated with 0.1 ml of RPMI containing 35,000 human umbilical vein endothelial cells (HUVECs) for 1.5 hours at 37° C. Unbound cells were decanted, and attached cells were stained with crystal violet and quantified by measuring their absorbance at 600 nm. C16Y exhibited the strongest inhibitory activity at all concentrations tested. Bars represent ±SD.

C16Y had the strongest inhibitory activity at all concentrations tested (FIG. 2). The most significant differences were observed at 50 µg/ml, where C16Y inhibited endothelial cell attachment to laminin-1 by >70%. C16 and C16S, on the other hand, inhibited by <40%. C16J had little activity at all of the doses tested, and C16L showed some inhibition at doses >75 µg/ml.

Example 3

Disruption of Endothelial Cell Tube Formation by C16Y

Tube-forming assays were performed as described previously (Ponce 2001). 48-well plates were coated with 200 μl/well of Matrigel (Gho 2001; Kubota 1988), a basement membrane matrix. HUVECs (24,000 cells/well) were plated in RPMI 1640 containing 10% bovine calf serum, defined and supplemented (HyClone Laboratories, Inc., Logan, Utah), along with 100 mg/liter of endothelial cell growth factor (Collaborative Biomedical). C16 or scrambled C16 peptides were added at concentrations ranging from 10-75 μg/ml. Control wells contained medium only. After 16 hours, cells were fixed and stained with Diff-Quick fixative (methanol) and solution II (6.25% (w/v) each of azure A and methylene blue) (Dade A G, Dudingen, Switzerland), and tube formation was scored by a blinded observer. Each peptide was tested at least in triplicate, and the assays were repeated a minimum of three times.

Figure 3:
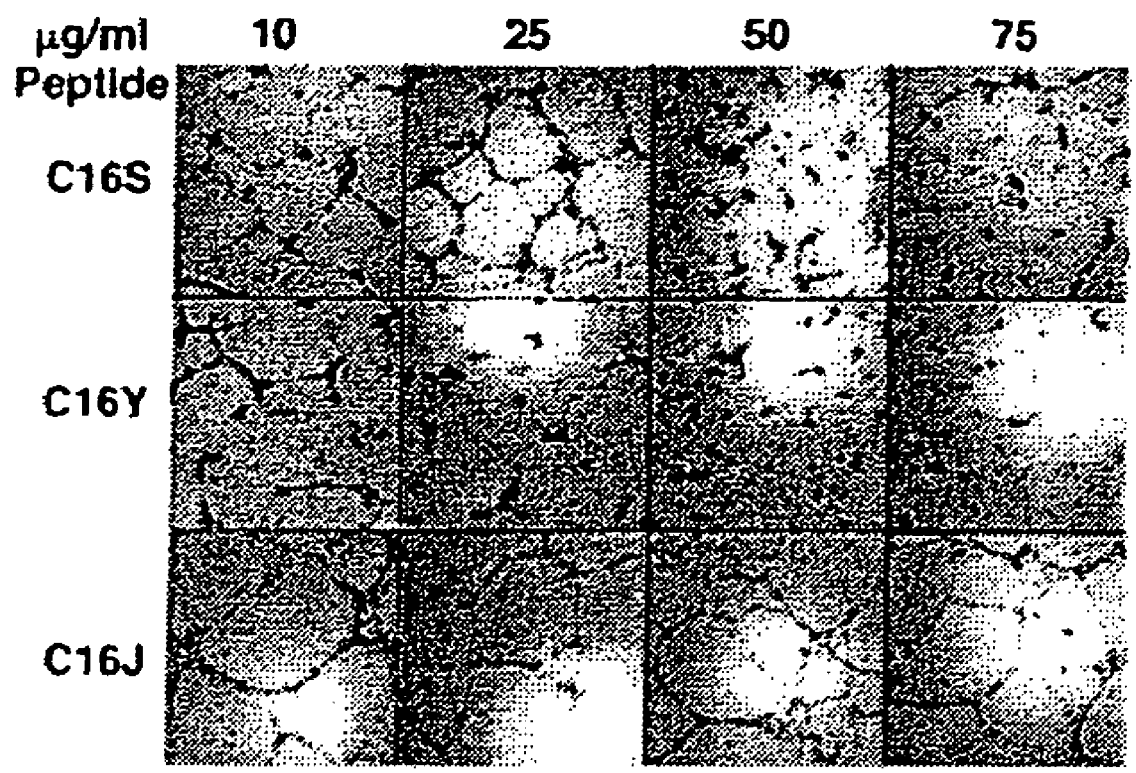
FIG. 3: Disruption of endothelial cell tube formation by C16Y peptide. 48-well plates were coated with 200 µl of Matrigel per well. Each well was treated with RPMI containing 24,000 human umbilical vein endothelial cells (HUVECS) and 100 mg/L endothelial cell growth factor in the presence of 10-75 µg/ml of C16 or scrambled C16 peptide for 16 hours. Control wells contained medium only. Cells were fixed and stained, and tube formation was scored by a blinded observer. C16Y exhibited the highest levels of disrupted tube formation at all concentrations tested, and disrupted tube formation at a lower concentration than any of the other peptides. C16J did not affect tube formation at any concentration.

As expected, C16 and C16S disrupted tube formation at 50 and 75 μg/ml, with little or no activity observed at lower doses (FIG. 3). In contrast, C16Y strongly disrupted tube formation at all of the doses tested, even those as low as 10 μg/ml. This dose is five times lower than that at which C16 or C16S are active. C16J, C16-3, and C16L, on the other hand, showed no activity at lower doses and only slight tube disruption at higher concentrations. Disruption of tube formation at varying peptide concentrations is summarized in the following table:

|         | Concentration (μg/ml) | | | |
|---------|----|-----|------|------|
| Peptide | 10 | 25  | 50   | 75   |
| C16     | −  | −   | +    | +++  |
| C16S    | −  | −   | +++  | +++  |
| C16J    | −  | −   | −    | −    |
| C16L    | −  | −   | +    | ++   |
| C16-3   | −  | −   | +    | +++  |
| C16Y    | ++ | +++ | ++++ | ++++ |

+, tubes slightly affected;
++ tubes moderately affected;
+++ tubes disrupted;
++++ tubes completely disrupted;
−, tubes resemble control Tube formation assays were repeated using truncated versions of the C16Y peptide to determine the minimal active sequence of the peptide. The carboxyl end of C16Y was not necessary for activity, whereas the amino terminal aspartic acid was required. The minimal active sequence for the C16Y peptide is shown in SEQ ID NO: 2. Each of the peptides containing at least this 8 amino acid sequence (SEQ ID NOs: 1-5) inhibited tube formation. The activity of each truncated peptide is summarized in the following table:

| Sequence     | Activity |
|--------------|----------|
| DFKLFAVYIKYR | ++       |
| FKLFAVYIKYR  | −        |
| KLFAVYIKYR   | −        |
| LFAVYIKYR    | −        |
| FAVYIKYR     | −        |
| AVYIKYR      | −        |
| VYIKYR       | −        |
| YIKYR        | −        |
| DFKLFAVYIKY  | ++       |
| DFKLFAVYIK   | ++       |
| DFKLFAVYI    | ++       |
| DFKLFAVY     | ++       |
| DFKLFAV      | −        |
| DFKLFA       | −        |
| DFKLF        | −        |
| DRKL         | −        |

Example 4

Inhibition of C16-Induced Angiogenesis by C16Y

The CAM assay was performed using 10-day-old embryonated eggs (CBT, Charlestown, Md.) as described previously (Gho 1999). On embryonal day 3, approximately 4 ml of ovalbumin was removed from each egg. After opening windows on embryonal day 10, the angiogenic stimulus (C16) and test competitor peptides in 5 μl of distilled water were applied to the CAM after drying on 13-mm diameter quartered plastic coverslips (Thermanox; Nalge, NUNC International, Naperville, Ill.). Three days later, the eggs were scored for a positive response and photographed. The positive control was bFGF, and the negative control was the vehicle water. Experiments were repeated twice using a minimum of 11 eggs for each data point.

Figure 4:
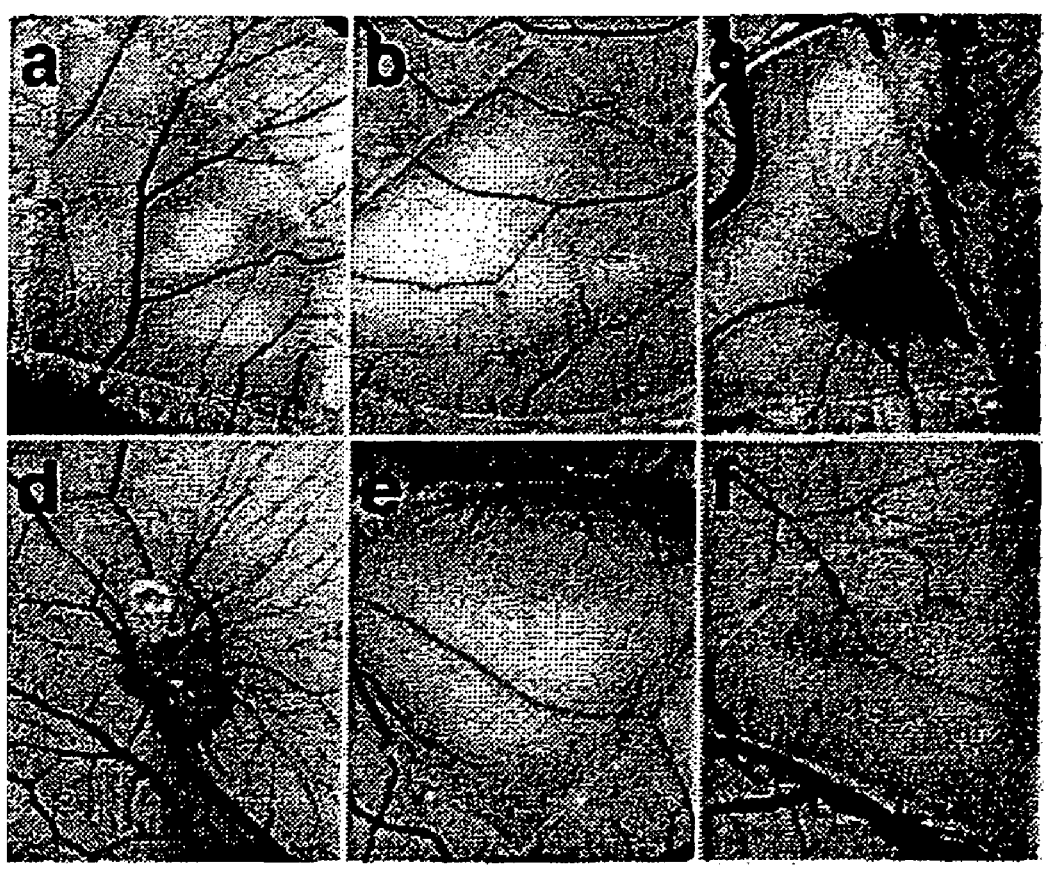
FIG. 4: Inhibition of C16-induced angiogenesis by C16Y. 0.5 µg of angiogenic stimulator (C16 peptide) and varying concentrations of either C16S or C16Y peptides were applied to 10-day-old embryonated eggs in 5 µl of water. After 3 days, microphotographs were taken of the eggs to determine angiogenesis levels. Negative control eggs were treated with water only (panel a), while positive control eggs were treated with bFGF only (not shown). As expected, C16 peptide administered alone stimulated angiogenesis (panel d). Angiogenesis was strongly inhibited in the presence of either 0.2 µg of C16S peptide (panel b) or 0.2 µg of C16Y peptide (panel e). When the amount of inhibitor peptide was lowered to 0.05 µg, C16Y peptide continued to inhibit angiogenesis (panel f), while C16S peptide had no effect (panel c).

As shown previously, 0.5 μg of C16 is capable of inducing angiogenesis in the chick CAM (FIG. 4, panel d). When a mixture containing 0.5 μg of C16 and 0.2 μg of either C16S (FIG. 4, panel b) or 0.2 μg C16Y inhibitory peptides (FIG. 4, panel e) was tested in the CAM assay, strong angiogenesis inhibition was observed. C16Y caused an 88% reduction in angiogenesis, while C16S caused a 63% reduction. When the amount of inhibitor peptide was lowered to 0.1 μg (one-fifth the amount of C16), C16Y caused a 75% reduction in angiogenesis, while C16S caused a 52% reduction. When the amount of inhibitor peptide was lowered to 0.05 μg (one-tenth the amount of C16), C16S no longer generated an inhibitory effect (FIG. 4, panel c). C16Y, on the other hand, continued to function as an angiogenesis inhibitor. 55% of the CAMs were weakly angiogenic in the presence of C16Y (FIG. 4, panel f). As expected, neither C16Y (FIG. 4, panel e) nor C16S (data not shown) administered alone stimulated angiogenesis. These results were similar to those of the control vehicle (FIG. 4, panel a).

Example 5

Figure 5:
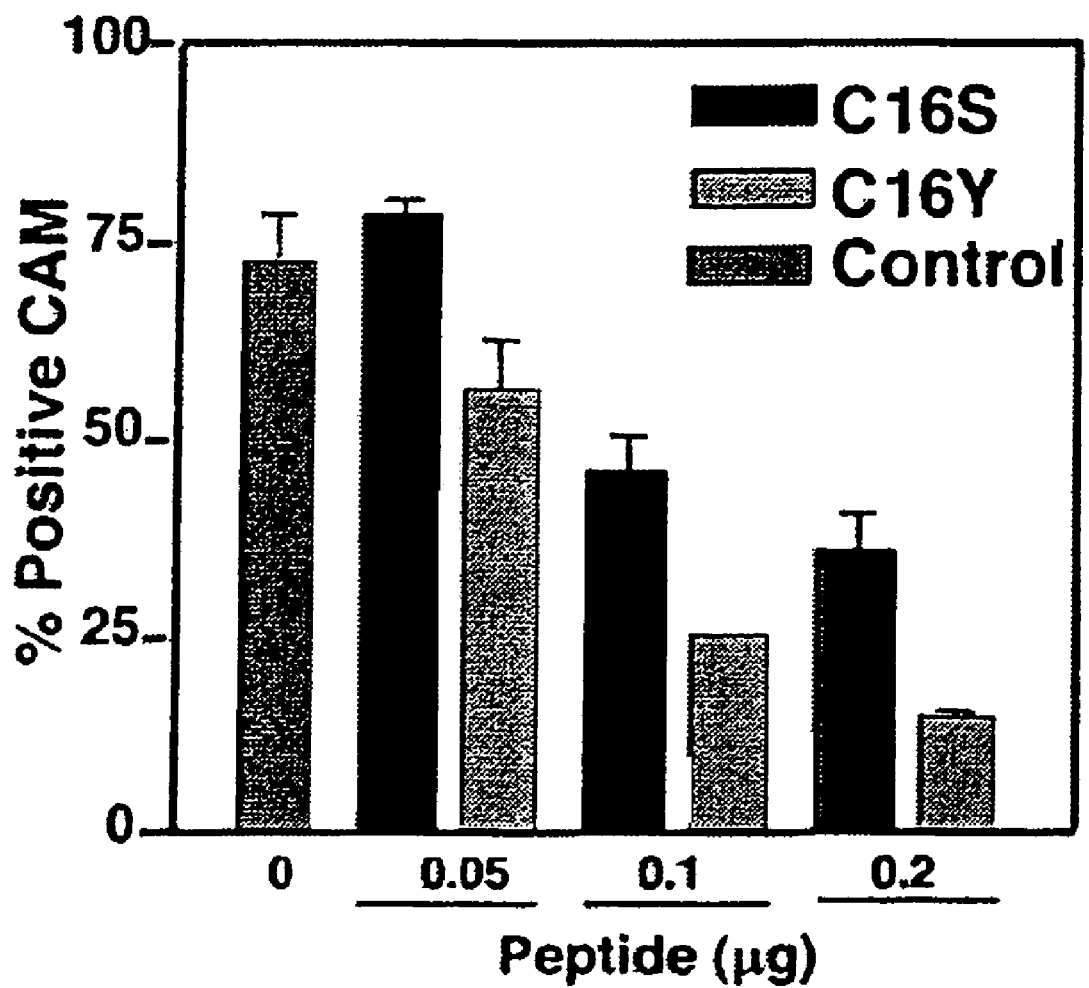
FIG. 5: Inhibition of bFGF-induced angiogenesis by C16Y. 50 ng of angiogenic stimulator (bFGF) and varying concentrations of either C16S or C16Y peptides were applied to 10-day old embryonated eggs in 5 µl of water, and CAMs were analyzed for the presence or absence of angiogenesis. C16Y inhibited angiogenesis more effectively than C16S at all concentrations tested, exhibiting inhibition at amounts as low as 0.05 µg. C16S displayed no ability to inhibit angiogenesis at that concentration.

Inhibition of bFGF-Induced Angiogenesis by C16Y 50 ng of angiogenic stimulator (bFGF) and varying concentrations of either C16S or C16Y peptides were applied to 10-day old embryonated eggs in 5 μl of water, and CAMs were analyzed after 3 days for the presence or absence of angiogenesis. C16Y inhibited angiogenesis more effectively than C16S at all concentrations tested, exhibiting inhibition at amounts as low as 0.05 μg (FIG. 5). C16S displayed no ability to inhibit angiogenesis at this low concentration.

Example 6

Inhibition of CAM Tumor Growth by C16Y

The effect of C16Y on tumor growth in vivo was analyzed using the CAM assay (Gho 2001). MDA-MB 231 breast tumor cells (a gift of Dan Welch, Pennsylvania State University, University Park, Pa.) ($1\times10^6$ cells/0.1 ml) in RPMI 1640 were mixed with 0, 50, or 100 μg/ml of C16 or C16Y, and then mixed 1:1 with a neutralized collagen I solution (4.6 mg/ml collagen type 1). This collagen I gel was overlayed with the CAM of a 7-day-old embryo. After a 7 day incubation, the membrane was fixed and tumor cells were removed and weighed. This experiment was repeated twice, with each data point tested in at least six replicates.

Figure 6:
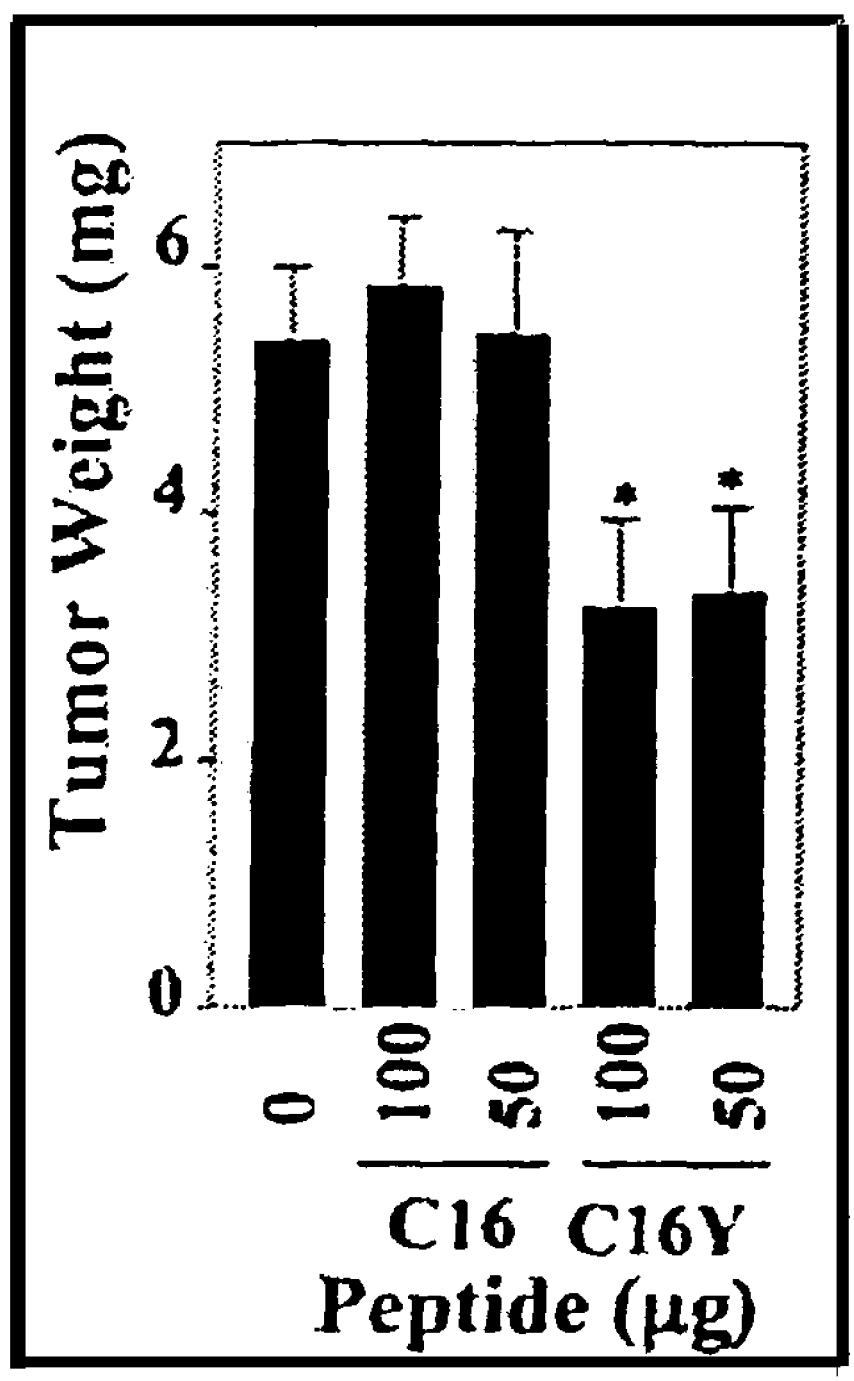
FIG. 6: Inhibition of CAM tumor growth by C16Y. MDA-MB 231 breast tumor cells were mixed with C16 or C16Y peptides (at either 50 or 100 µg/ml), then mixed with 1:1 with neutralized collagen I solution. The collagen I gel was overlayed with the CAM of a 7-day-old embryo for 7 days, after which the membrane was fixed and tumor cells were removed and weighed. In the absence of either peptide, average tumor weight was 5.40±0.59 mg. C16 peptide did not significantly affect tumor growth at either concentration. C16Y peptide inhibited tumor growth by approximately 40% at both concentrations tested. Bars represent ±SD.

Results of this assay are summarized in FIG. 6. In the absence of peptide, the tumor grew to an average weight of 5.40±0.59 mg. The presence of either 50 or 100 μg/ml of the angiogenic peptide C16 did not considerably affect tumor growth (5.45±0.84 mg and 5.85±0.54 mg, respectively). At both 50 and 100 μg/ml, C16Y inhibited tumor growth by approximately 40% ($P<0.05$). More vessels were observed in untreated tumors and tumors treated with C16 than in tumors treated with C16Y (7.5±0.45 versus 9.6±0.23 versus 5.1±0.16; $P\leq0.027$).

Example 7

Effect of C16Y on Tumor Cell Proliferation

A proliferation assay was performed to determine whether the tumor inhibition discussed in Example 6 was the result of angiogenesis inhibition or some effect on cell proliferation. Proliferation of MDA-MB 231 cells was quantified using a Cell Titer 96 Aqueous Cell Proliferation assay kit (Promega, Madison, Wis.). Cells were plated on four 96-well dishes at $5\times10^3$ cells/well and cultured in AIM-V serum-free medium (Life Technologies, Inc., Gaithersburg, Md.). After 1 hour, peptides C16 and C16Y were added at a final concentration of 100 μg/ml. A separate dish was used to quantitate proliferation at 2, 24, 48, and 72 hours by reading absorbance at 490 nm on an Emax plate reader. Each experiment was repeated in triplicate two times.

Neither C16 nor C16Y altered MDA-MB 231 cell proliferation, suggesting that inhibition of tumor growth by C16Y is due to its ability to inhibit angiogenesis (data now shown).

Example 8

Inhibition of Primary Tumor Growth by C16Y

MDA-MB 231 breast cancer cells ($5\times10^5$ cells) mixed with Matrigel (1:4) were injected subcutaneously (s.c.) into nude mice. Within 7-9 days after injection, breast carcinoma tumors reached a volume of 200-300 mm³. Mice were then administered C16 or C16Y peptide on a daily basis by intraperitoneal (i.p.) injection. Control mice were injected daily with vehicle only (water). Tumor growth was monitored with a caliper, with measurements being taken on days 0, 3, 6, and 9 after the first peptide injection. Tumor volume was determined using the formula width²×length×0.52. At the end of the experiments, tumors were excised, weighed, and fixed with formalin. Vessel number was determined by staining sections with a CD-31 antibody (Nomizu 2001) and counting 6 fields per section per mouse (n=2 section/mouse; total 3 mice).

Figure 7:
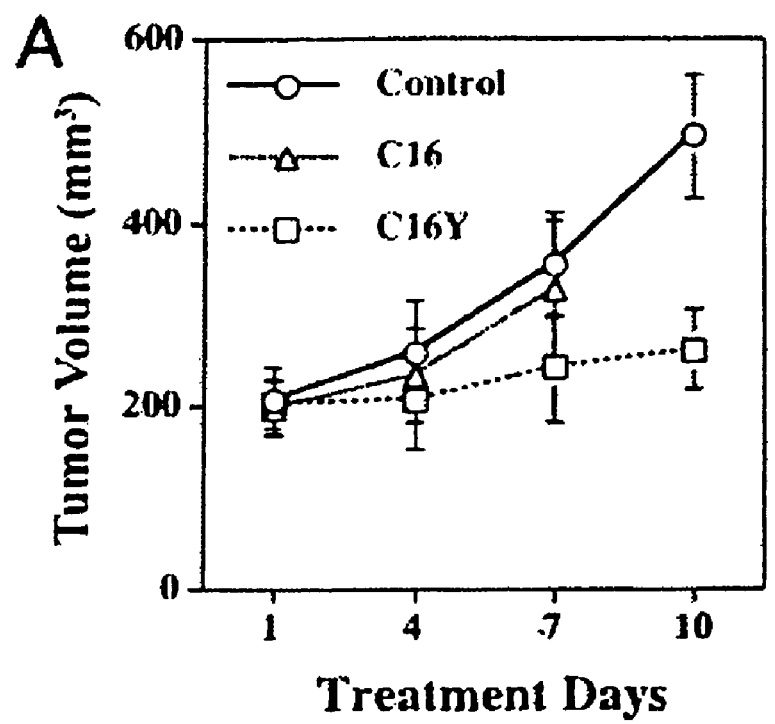
FIG. 7: Inhibition of primary tumor growth by C16Y. MDA-MB 231 cancer cells were injected subcutaneously (s.c.) into nude mice and the tumors were allowed to grow until they reached 200-300 mm$^3$. Mice were then treated daily for 7-10 days with C16 (1 mg/day) or C16Y peptides (0.2, 0.5, or 1 mg/day) by intraperitoneal (i.p.) injection. Control mice were injected with water only. Tumor size was measured at 0, 3, 6, and 9 days after peptide injections began. A. Mice were treated with 1 mg/day of either C16 or C16Y peptide for 10 days. Tumor growth in mice treated with C16Y peptide was significantly inhibited, while tumor growth in mice treated with C16 peptide was similar to that of control mice. B. Mice were treated with C16Y peptide at varying concentrations for 7 days. C16Y decreased tumor size at all concentrations tested during the 7 days it was administered. Tumor growth resumed when administration of the C16Y peptide was halted, with tumor size increasing more rapidly in mice treated with lower dosages of C16Y. Bars represent ±SD.
Figure 7:
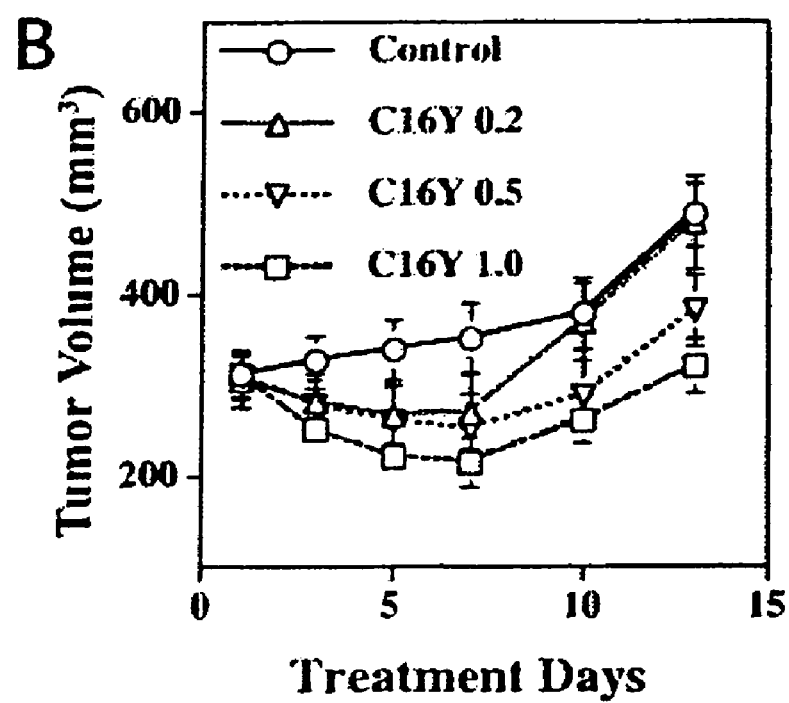

In one experiment, mice were treated with 1 mg/day of either C16 or C16Y peptide for 10 days. After 7 days, tumor growth was significantly inhibited ($P<0.028$) in mice treated with C16Y (FIG. 7A). In contrast, tumors in control mice and those treated with C16 grew to 1.7-2.5 times their original size over that same time period. Although it was expected that C16 tumors would grow more rapidly than control tumors, it was interesting to note that C16 treatment did not significantly affect tumor growth. This may be explained by the production of high levels of growth factors that are endogenously secreted by the tumor itself.

In a second experiment, mice were treated with varying concentrations of C16Y peptide (0.2, 0.5, or 1 mg/day) for 7 days. Treatment with C16Y peptide reduced tumor size over the 7-day administration period at all concentrations tested (FIG. 7B). In mice receiving a dosage of 1 mg/day, tumor size was reduced by approximately 33%. However, when daily administration of C16Y peptide was stopped on day 7, the tumors began to grow rapidly (FIG. 7B). The tumors grew fastest in those mice that had been treated with the lowest C16Y dose (0.2 mg), approaching control mice tumor volumes within 3 days. Tumors in mice that received 0.5 mg/day of C16Y peptide grew more slowly, while tumors in mice that had received 1 mg/day of C16Y peptide took approximately 6 days to reach initial tumor size. These results strongly suggest that C16Y can reduce tumor growth via its antiangiogenic activity.

Example 9

Inhibition of Choroidal Neovascularization by C16Y In Vivo

Figure 8:
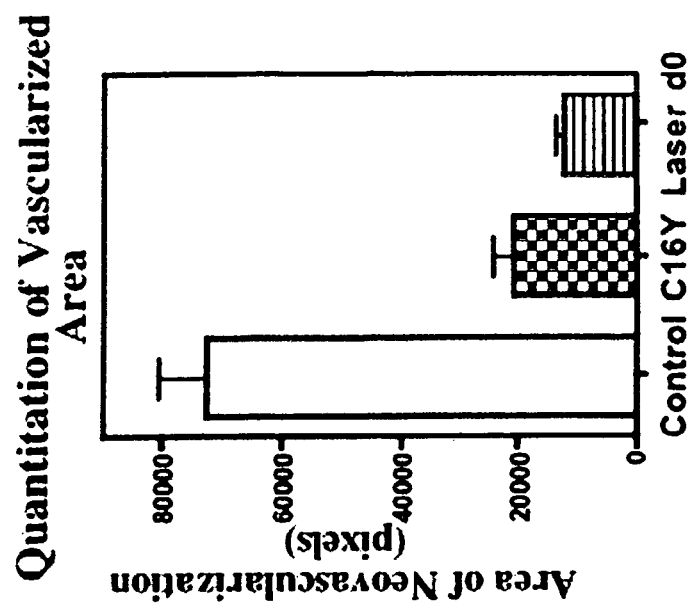
FIG. 8: Inhibition of choroidal neovascularization by C16Y peptide in vivo. Choroidal neovascularization (CN) was induced in C57/BL6 mice by making four separate burn choroidal lesions with a diode laser in areas adjacent to the optic nerve. Mice were treated daily for 14 days with C16Y peptide (1 mg in 100 µl of carrier) by intraperitoneal (i.p.) injection. Control mice were injected with an irrelevant peptide (C18) or carrier only. After 14 days, mice were sacrificed and eyes were enucleated and prepared for posterior pole examination. Choroids were examined by microscopy, and lesion areas were quantitated using Adobe PhotoShop. A. Substantial CN was observed in control mice (left panels), while mice treated with C16Y displayed a statistically significant decrease in CN (center panels). The right panel illustrates CN in untreated mice immediately after laser burning. B. The average area of neovascularization in control mice was over 70,000 pixels, versus approximately 20,000 pixels for mice treated with C16Y peptide. The average area of neovascularization immediately after laser burning (d0) was approximately 14,000 pixels.
Figure 8:
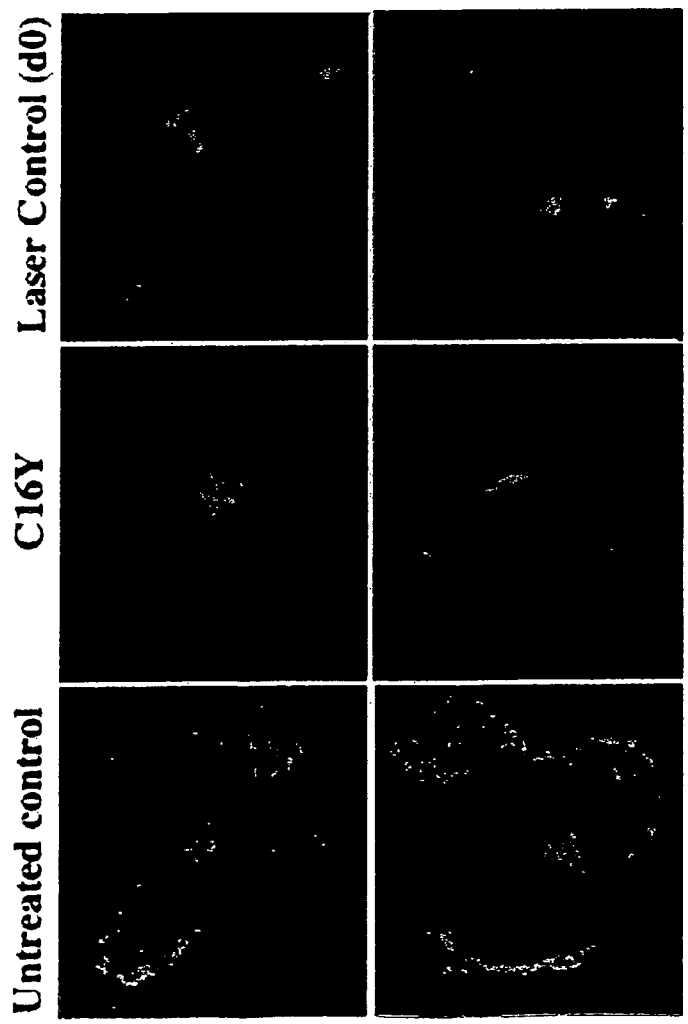

The effect of C16Y administration on CN was tested using C57/BL6 mice. CN was induced by making four separate burn choroidal lesions in areas adjacent to the optic nerve using a diode laser. For restraining purposes, mice were anesthetized with a ketamine/xylosine mixture. Mice were subdivided into several groups of 4-6. The first group was treated with C16Y, while the two control groups were treated with an irrelevant peptide (C18) or carrier only (water). Treatments were administered daily by intraperitoneal injection, at a dosage of 1 mg peptide in 100 μl carrier. After 14 days of treatment, mice were sacrificed and lesions were visualized by perfusing each mouse with 5 ml of PBS, 4% PFA, and 1.2 ml of a solution consisting of 10 mg/ml of $2\times10^6$ $M_W$ FITC-dextran and $4\times10^6$ $M_W$ FITC-dextran in a 2:1 ratio. Eyes were enucleated and flatmounts were prepared for posterior pole examination. Choroids were examined by microscopy, and lesion areas were quantitated using Adobe PhotoShop. Other controls included eyes of untreated mice at d=0 to quantify the starting size of the lesion. Results of the CN assays are summarized in FIG. 8. In control mice, substantial CN was observed. Mice treated with C16Y, on the other hand, displayed a statistically significant decrease in CN (FIG. 8a). The average area of neovascularization in control mice was over 70,000 pixels, versus approximately 20,000 pixels for C16Y treated mice (FIG. 8b). The average area of neovascularization in untreated mice at d=0 was approximately 14,000 pixels.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. Elements or features of one embodiment may of course be used in other embodiments. All references cited herein are incorporated by reference as if fully set forth herein.

Abbreviations used herein: ECM, extracellular matrix; CN, choroidal neovascularization; AMD, age-related macular degeneration; CAM, chick chorioallantoic membrane; HUVEC, human umbilical vein endothelial cell; bFGF, basic fibroblast growth factor; VEGF, endothelial growth factor; BSA, bovine serum albumin; PBS, phosphate buffer saline.

REFERENCES

1. Auerbach, R., et al. 1985. Expression of organ-specific antigens on capillary endothelial cells. Microvasc Res 29:401-411.
2. Brooks, P. C., Clark, R. A., Cheresh, D. A. 1994. Requirement of vascular integrin αvβ3 for angiogenesis. Science (Wash D.C.) 264:569-571.
3. Burgeson, R. E., et al. 1994. A new nomenclature for the laminins. Matrix Biol 14:209-211.
4. C-elegans consortium. Genome sequence of the nematode c. elegans: a platform for investigating biology. Science 282:2012-2018.
5. Ciulla, T. A. 2003. Recent advances in the treatment of exudative age-related macular degeneration, including transpupillary thermotherapy. Acta Opthalmol Scand 81:103-104.
6. Colognato, H., Yurchenco, P. D. 2001. Form and function: the laminin family of heterotrimers. Dev Dyn 218:213-234.
7. Fisher, C., et al. 1996. Treatment of septic shock with the tumor necrosis factor receptor:Fc fusion protein. The Soluble TNF Receptor Sepsis Study Group. N Engl J Med 334:1697-1702.
8. Folkman, J. 1995. Angiogenesis in cancer, vascular, rheumatoid and other diseases. Nat Biotechnol 1:27-31.
9. Francis, G. E. 1992. Protein modification and fusion proteins. Focus on Growth Factors 3:4-10.
10. Fridman, R., et al. 1990. Reconstituted basement membrane (matrigel) and laminin can enhance the tumorigenicity and the drug resistance of small cell lung cancer cell lines. Proc Natl Acad Sci USA 87:6698-6702.
11. Friedlander, M., et al. 1995. Definition of two angiogenic pathways by distinct a v integrins. Science (Wash D.C.) 270:1500-1502.
12. Fujihara, S. M., et al. 2000. A D-amino acid peptide inhibitor of NF-κB nuclear localization is efficacious in models of inflammatory disease. J Immunol 165:1004-1012.
13. Gho, Y. S., Kleinman, H. K., Sosne, G. 1999. Angiogenic activity of human soluble intercellular adhesion molecule-1. Cancer Res 59:5128-5132.
14. Gho, Y. S., et al. 2001. Stimulation of tumor growth by human soluble intercellular adhesion molecule-1 (sICAM-1). Cancer Res 61:4253-4257.
15. Grant, D. S., et al. 1989. Two different laminin domains mediate the differentiation of human endothelial cells into capillary-like structures in vitro. Cell 58:933-943.
16. Harvill, E. T., Morrison, S. L. 1995. An IgG3-IL2 fusion protein activates complement, binds Fc gamma RI, generates LAK activity and shows enhanced binding to the high affinity IL-2R. Immunotechnology. 1995 August; 1 (2):95-105.
17. Iivanainen, E., Kahari, V. M., Heino, J., Elenius, K. 2003. Endothelial cell matrix interactions. Microsc Res Tech 60:13-22.
18. Iwamoto, Y., et al. 1987. YIGSR a pentapeptide from the B1 chain of laminin inhibits tumor cell metastases. Science 238:1132-1134.
19. Jaffe, E. A., Nachman, R. L., Becker, C. G., and Minick, C. R. 1973. Culture of human endothelial cells derived from umbilical veins. Identification by morphologic and immunologic criteria. J Clin Investig 52:2745-2756.
20. Kleinman, H. K., Koblinski, J., Lee, S., Engbring, J. Role of basement membrane in tumor growth and metastasis. Surg Oncol Clin N Am 10:329-338.
21. Kohner, E. M., Oakeley, N. W. 1975. Diabetic retinopathy. Metabolism 24:1085-1102.
22. Kubota, Y., Kleinman, H. K., Martin, G. R., Lawley, T. J. 1988. Role of laminin and basement membrane in the differentiation of human endothelial cells into capillary-like structures. J Cell Biol 107:1589-1597.
23. Kuratomi, Y., et al. 2002. Laminin γ1 chain peptide, C-16 (KAFDITYVRLKF), promotes migration, MMP-9 secretion, and pulmonary metastasis of B16-F10 mouse melanoma cells. Br J Cancer 86:1169-1173.
24. Kuratomi, Y., et al. 1999. Identification of metastasis-promoting sequences in the mouse laminin α-1 chain. Exp Cell Res 249:386-395.
25. Lehoux, S., Tedgui, A. 2003. Cellular mechanics and gene expression in blood vessels. J Biomech 36:631-643.
26. Maeshima, Y., et al. 2001. Extracellular matrix derived peptide binds to αvβ3 integrin and inhibits angiogenesis. J Biol Chem 276:31959-31968.
27. Malinda, K. M., et al. 1999. Identification of laminin α-1 and β-1 chain peptides active for endothelial cell adhesion, tube formation, and aortic sprouting. FASEB J 13:53-62.
28. Miner, J. H., et al. 1997. The laminin α chains: expression, developmental transitions, and chromosomal location of α1-5, identification of heterotrimeric laminins 8-11, and cloning of a novel α3 isoform. J Cell Biol 137:685-701.
29. Nomizu, M., et al. 1995. Identification of cell binding sites in the laminin al chain carboxyl-terminal globular domain by systematic screening of synthetic peptides. J Biol Chem 270:20583-20590.
30. Nomizu, M., et al. 1997. Identification of cell binding sequences in mouse laminin γ-1 chain by systematic peptide screening. J Biol Chem 272:32198-32205.
31. Nomizu, M., et al. 1998. Cell binding sequences in mouse laminin al chain. J Biol Chem 273:32491-32499.
32. Nomizu, M., et al. 2001. Identification of homologous biologically active sites on the N-terminal domain of laminin α chains. Biochemistry 40:15310-15317.
33. O'Reilly, M. S., et al. 1994. Angiostatin: a novel angiogenesis inhibitor that mediates the suppression of metastases by a Lewis lung carcinoma. Cell 79:315-328.
34. O'Reilly, M. S., et al. 1997. Endostatin: an endogenous inhibitor of angiogenesis and tumor growth. Cell 24:277-285.
35. Pepper, M. S. 2001. Role of matrix metalloproteinases and plasminogen activator-plasmin in angiogenesis. Arterioscler Thromb Vasc Biol 21:1104-1117.
36. Plendl, J., et al. 1996. Isolation and characterization of endothelial cells from different organs of fetal pigs. Anat Embrol 194:445-456.

37. Ponce, M. L., et al. 1999. Identification of endothelial cell binding sites on the laminin γ-1 chain. Circ Res 84:688-694.
38. Ponce, M. L., Nomizu, M., Kleinman, H. K. 2001. An angiogenic laminin site and its antagonist bind through the αvβ3 and α5β1 integrins. FASEB J 15:1389-1397.
39. Ponce, M. L., Kleinman, H. K. 2003a. Redundant site in laminin α1 and γ1 chains are angiogenic in vivo via integrins α5β1 and αVβ3. Exp Cell Res 285:189-195.
40. Ponce, M. L., et al. 2003b. Identification of a potent peptide antagonist to an active laminin-1 sequence that blocks angiogenesis and tumor growth. Cancer Res 63:5060-5064.
41. Powell, S. K., Kleinman, H. K. 1997. Neuronal laminins and their cellular receptors. Int J Biochem Cell Biol 29:401-414.
42. Pupa, S. M., Menard, S., Forti, S., Tagliabue, E. 2002. New insights into the role of extracellular matrix during tumor onset and progression. J Cellul Physiol 192:259-267.
43. Rattan, S. I., Derventzi, A., Clark, B. F. 1992. Protein synthesis, posttranslational modifications, and aging. Ann AIYA Sci 663:48-62.
44. Risau, W. 1997. Mechanisms of angiogenesis. Nature (Lond.) 386:671-674.
45. Sakamoto, N., Iwahana, M., Tanaka, N. G., Osada, Y. 1991. Inhibition of angiogenesis and tumor growth by a synthetic laminin peptide, CD PGYIGSR-NH2. Cancer Res 51:903-906.
46. Seifter, S., Englard, S. 1990. Analysis for protein modifications and nonprotein cofactors. Meth Enzymol 182:626-646.
47. Treatment of age-related macular degeneration with photodynamic therapy (TAP) study group. 1999. Photodynamic therapy of subfoveal choroidal neovascularization in age-related macular degeneration with verteporfin: one-year results of 2 randomized clinical trials—TAP report. Arch Opthalmol 117(10):1329-1345.
48. Taraboletti, G., et al. 2000. The heparin binding 25 kDa fragment of thrombospondin-1 promotes angiogenesis and modulates gelatinase and TIMP-2 production in endothelial cells. FASEB J 14:1674-1676.
49. Timpl, R., Brown, J. C. 1994. The laminins. Matrix Biol 14:275-281.
50. Tolsma, S. S., et al. 1993. Peptides derived from two separate domains of the matrix protein thrombospondin-1 have anti-angiogenic activity. J Cell Biol 122:497-511.
51. Varner, J. A., Cheresh, D. A. 1996. Tumor angiogenesis and the role of vascular cell integrin αvβ3. Important Adv Oncol 69-87.
52. Votruba, M., Gregor, Z. 2001. Neovascular age-related macular degeneration: present and future treatment options. Eye 15(Pt. 3):424-429.
53. Wang, H. H., Nance, D. M., Orr, F. W. 1999. Murine hepatic microvascular adhesion molecule expression is inducible and has a zonal distribution. Lin Exp Metastasis 17:149-155.
54. Wilhelmi, M., et al. 2002. Endothelial anatomy of the human heart: immunohistochemical evaluation of endothelial differentiation. Thorac Cardiovasc Surg 50:230-236.
55. Zheng, X., et al. 1995. Administration of noncytolytic IL-10/Fc in murine models of lipopolysaccharide-induced septic shock and allogeneic islet transplantation. J of Immunol 154:5590-5600.

What is claimed is:

1. A pharmaceutical composition comprising a peptide comprising the amino acid sequence of SEQ ID NO: 1.

2. A pharmaceutical composition comprising a peptide comprising the amino acid sequence of SEQ ID NO: 2, SEQ ID NO: 3, SEQ ID NO: 4, or SEQ ID NO: 5.

3. The pharmaceutical composition of claim 1 or claim 2, wherein the peptide further comprises a modification selected from pegylation, biotinylation, acetylation, ubiquitination, amidation, a radiolabel, an Fc antibody, and one or more D form amino acids.

4. The pharmaceutical composition of claim 3, wherein the peptide is modified by addition of an Fc antibody or by pegylation.

5. The pharmaceutical composition of claim 3, wherein the peptide comprises one or more D form amino acids.

6. The pharmaceutical composition of claim 3, wherein the peptide comprises an N-terminal amide.

7. A kit comprising (a) a composition comprising a peptide comprising the amino acid sequence of SEQ ID NO: 1, SEQ ID NO: 2, SEQ ID NO: 3, SEQ ID NO: 4, or SEQ ID NO: 5 and (b) instructions for administration of the composition.

8. The kit of claim 7, wherein the peptide further comprises a modification selected from pegylation, biotinylation, acetylation, ubiquitination, amidation, a radiolabel, an Fc antibody, and one or more D form amino acids.

9. The kit of claim 8, wherein the peptide is modified by addition of an Fc antibody or by pegylation.

10. The kit of claim 8, wherein the peptide comprises one or more D form amino acids.

11. The kit of claim 8, wherein the peptide comprises an N-terminal amide.

12. The kit of claim 7, wherein the peptide comprises the amino acid sequence of SEQ ID NO: 1.

13. The kit of claim 7, wherein the peptide comprises the amino acid sequence of SEQ ID NO: 2.

14. The kit of claim 7, wherein the peptide comprises the amino acid sequence of SEQ ID NO: 3.

15. The kit of claim 7, wherein the peptide comprises the amino acid sequence of SEQ ID NO: 4.

16. The kit of claim 7, wherein the peptide comprises the amino acid sequence of SEQ ID NO: 5.

17. The composition of claim 2, wherein the peptide comprises the amino acid sequence of SEQ ID NO: 2.

18. The composition of claim 2, wherein the peptide comprises the amino acid sequence of SEQ ID NO: 3.

19. The composition of claim 2, wherein the peptide comprises the amino acid sequence of SEQ ID NO: 4.

20. The composition of claim 2, wherein the peptide comprises the amino acid sequence of SEQ ID NO: 5.

* * * * *

UNITED STATES PATENT AND TRADEMARK OFFICE
CERTIFICATE OF CORRECTION

| | |
|---|---|
| PATENT NO. | : 8,039,585 B2 |
| APPLICATION NO. | : 10/588884 |
| DATED | : October 18, 2011 |
| INVENTOR(S) | : Csaky et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1382 days.

Signed and Sealed this
Sixteenth Day of October, 2012

David J. Kappos
*Director of the United States Patent and Trademark Office*